(12) United States Patent
Tedder

(10) Patent No.: US 6,921,846 B1
(45) Date of Patent: Jul. 26, 2005

(54) ANTIBODY PRODUCTION METHODS RELATING TO DISRUPTION OF PERIPHERAL TOLERANCE IN B LYMPHO-CYTES

(75) Inventor: Thomas F. Tedder, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/555,349

(22) PCT Filed: Nov. 25, 1998

(86) PCT No.: PCT/US98/25253

§ 371 (c)(1),
(2), (4) Date: Aug. 1, 2000

(87) PCT Pub. No.: WO99/27963

PCT Pub. Date: Jun. 10, 1999

Related U.S. Application Data

(60) Provisional application No. 60/065,975, filed on Nov. 28, 1997.

(51) Int. Cl.[7] .......................... C12P 21/00; A01K 67/00; A01K 67/027
(52) U.S. Cl. .................... 800/4; 800/5; 800/6; 800/13; 800/18
(58) Field of Search .................... 800/4–18; 424/93.21, 424/184.1; 435/325, 326

(56) References Cited

U.S. PATENT DOCUMENTS

| 5,223,410 A | 6/1993 | Gargan et al. |
| 5,675,063 A | 10/1997 | Knight et al. |

FOREIGN PATENT DOCUMENTS

| WO | WO 96/14401 | * 11/1995 |

OTHER PUBLICATIONS

Engel et al, Immunity 1995;3:39–50.*
Nielsen et al, EMBO J 1983;2:115–9.*
Mullins et al. Perspectives series: Molecular medcine in genetically engineered animals pp. 1557–1562 1996 vol. 97, No. 7.*
Hammer et al. Genetic engineering of mammalian embryos pp. 269–278 Jul. 1986.*
Wall et al. Transgenic dairy cattle: genetic engineering on a large scale pp. 2213–2224 1997.*
A Strasser et al., Proc. Natl. Acad. Sci, USA, "Enforced BCL2 expression in B–lymphoid cells prolongs antibody responses and elicits autoimmune disease," Oct. 1991, vol. 88, pp. 8661–8665.*

GJ Hammerling et al., Proc. Natl. Sci USA, "Self–tolerance to HLA focuses the response of immunized HLA–transgenic mice on production of antibody to precise polymorphic HLA alloantigens," Jan. 1990, vol. 87, pp. 235–239.*

S Yoshino et al., European Journal of Pharmacology, "Effect of a monoclonal antibody against interleukin–4 on the induction of oral tolerance in mice," Oct. 1997, 336: 203–209.*

Bohlen et al., "Cytolysis of Leukemic B–Cells by T–Cells Activated via Two Bispecific Antibodies," Cancer Research, p. 4310–4314, (Sep. 15, 1993).

Burnett et al., "Human Monoclonal Antibodies to Defined Antigens," Human Hybridomas and Mab, Plenum Press, p. 113–133, (1985).

Brink et al., "Immunoglobulin M and D Antigen Receptors are Both Capable of Mediating B Lymphocyte Activation, Deletion, to Energy After Interaction with Specific Antigen," J. Exp. Med., p. 991–1005, (Oct. 1992).

Sato et al., "CD19 Regulates B Lymphocyte Signaling Thresholds Critical for the Development of B–1 Lineage Cells and Autoimmunity," J. Immunology, vol. 157, p. 4371–4378, (1996).

Zhou et al., "Tissue–Specific Expression of the Human CD19 Gene in Transgenic Mice Inhibits Antigen–Independent B–Lymphocyte Development," Molecular and Cellular Biology, vol.14 (No. 6), p. 3884–3894, (Jun., 1994).

PCT International Search Report dated Mar. 2, 1999 for corresponding PCT application No. PCT/US98/25253.

Tedder et al., "The CD19–CD21 Complex Regulates Signal Review Transduction Thresholds Governing Humoral Immunity and Autoimmunity," Immunity, vol. 6, p. 107–118, (Feb., 1997).

* cited by examiner

Primary Examiner—Q. Janice Li
(74) Attorney, Agent, or Firm—Jenkins, Wilson & Taylor, P.A.

(57) ABSTRACT

The subject invention relates a method for the production of monoclonal antibodies. The method utilizes an immunized animal having antibody-producing cells with disrupted peripheral tolerance. The invention also provides a method for the use of such monoclonal antibodies, and polyclonal antibodies derived from an immunized animal having antibody-producing cells with disrupted peripheral tolerance, for in vitro and in vivo clinical diagnostics and therapeutics.

2 Claims, 6 Drawing Sheets

ANTIBODY PRODUCTION METHODS RELATING TO DISRUPTION OF PERIPHERAL TOLERANCE IN B LYMPHO-CYTES

PRIORITY APPLICATION INFORMATION

This application is a regular United States patent application under 37 C.F.R. § 1.111(a) based on and claiming priority to U.S. Provisional Application Ser. No. 60/065,975 filed Nov. 28, 1997, the entire contents of which are herein incorporated by reference.

GRANT STATEMENT

This invention was made in part from government support under Grant Number AI-26872 from the National Institute of Health (NIH). The U.S. Government has certain rights in the invention.

TECHNICAL FIELD OF THE INVENTION

The subject invention relates generally to a method for the production of monoclonal antibodies. More particularly, the subject invention utilizes an animal having antibody-forming cells, such as B lymphocytes, with disrupted peripheral tolerance. Preferably, the animal comprises a transgenic animal. The invention also provides a method for the use of such monodonal antibodies, and polyclonal antibodies derived from an animal having antibody-forming cells, such as B lymphocytes, with disrupted peripheral tolerance, for in vitro and in vivo clinical diagnostics and therapeutics.

The publications and other materials used herein to illuminate the background of the invention, and in particular cases, to provide additional details respecting the practice, are incorporated herein by reference, and for convenience, are referenced by author and date in the following text, and respectively group in the appended list of references.

Table of Abbreviations

Ab—antibody
AFC—antibody-forming cell
Ag—antigen
ALP—alkaline phosphatase
BSA—bovine serum albumin
Btk—Bruton's tyrosine kinase
C—complement, usually followed by a number from 1 to 9 when referencing the factors of the complement system in the immune system
CD—cluster of differentiation
CD19—cell surface molecule of B lymphocytes
CD19KO—CD19-deficient mice
CD19TG—human CD19-transgenic mice
CFA—complete Freund's adjuvant
CGG—chicken gamma-globulin
CJD—Creutzfeldt-Jakob disease
15B3—a monoclonal antibody against bovine, murine and human prion protein epitope
HAT—hypoxanthine, aminopterin and thymidine
hCD19—human CD19
HPRT—hypoxanthine phosphoribosyl transferase
HRP—horseradish peroxidase
Ig—immuoglobulin
$Ig^{HEL}$—high-affinity HEL-specific $IgM^a$ and $IgD^a$-antigen receptors
Lyn—a tyrosine kinase
MAb—monoclonal antibody
MHC—major histocompatability complex
NP—(4-hydroxy-3-nitrophenyl)acetyl
PNA—peanut agglutinin
PrP—prion protein
PrPc—a normal prion protein epitope
PrPSc—a disease related prion protein epitope
sHEL—soluble hen egg lysozyme
TSE—transmissible spongiform encephalopathic agents
TUNEL—terminal deoxynucleotidyl transferase (TdT)-mediated dUTP-biotin nick-end labeling
Vav—a protooncogene
Xid—X-linked immunodeficiency—a mutation in Btk

BACKGROUND OF THE INVENTION

Kohler and Milstein are generally credited with having devised the techniques that successfully resulted in the formation of the first monoclonal antibody-producing hybridomas (G. Kohler and C. Milstein (1975) *Nature* 256:495–497; (1976), *Eur. J. Immunol.* 6:511–519). By fusing antibody-forming cells (spleen B-lymphocytes) with myeloma cells (malignant cells of bone marrow primary tumors), they created a hybrid cell line arising from a single fused cell hybrid (called a hybridoma or clone). The hybridoma had inherited certain characteristics of both the lymphocytes and the myeloma cell lines. Like the lymphocytes, the hybridoma secreted a single type of immunoglobulin; moreover, like the myeloma cells, the hybridoma had the potential for indefinite cell division. The combination of these two features offered distinct advantages over conventional antisera.

Antisera derived from vaccinated animals are variable mixtures of polyclonal antibodies which never can be reproduced identically. Monoclonal antibodies are highly specific immunoglobulins of a single type. The single type of immunoglobulins secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6–7 amino acids in length; Atassi, M. Z. (1980) *Molec. Cell. Biochem.* 32:21–43) within the entire protein molecule. Hence, monoclonal antibodies raised against a single antigen may be distinct from each other depending on the determinant that induced their formation. For any given hybridoma, however, all of the antibodies it produces are identical. Furthermore, the hybridoma cell line is easily propagated in vitro or in vivo, and yields monoclonal antibodies in extremely high concentration.

A monoclonal antibody can be utilized as a probe to detect its antigen. Thus, monoclonal antibodies have been used in in vitro diagnostics, for example, radioimmunoassays and enzyme-linked immunoassays (ELISA), and in in vivo diagnostics, e.g. in vivo imaging with a radio-labeled monoclonal antibody. Also, a monoclonal antibody can be utilized as a vehicle for drug delivery to such antibodies' antigen.

Before a monoclonal antibody can be utilized for such purpose, however, it is essential that the monoclonal antibody be capable of binding to the antigen of interest; i.e., the target antigen. This procedure is carried out by screening the hybridomas that are formed to determine which hybridomas, if any, produce a monoclonal antibody that is capable of binding to the target antigen. This screening procedure can be very tedious in that numerous, for example, perhaps several thousand monoclonal antibodies may have to be screened before a hybridoma that produces an antibody that is capable of binding the target antigen is identified. Accordingly, there is a need for a method for the production of monoclonal antibodies that increases the likelihood that the hybridoma will produce an antibody to the target antigen.

Additionally, the immune systems of conventional animals used in the production of monoclonal antibodies cannot recognize epitopes that are highly conserved among vertebrate, and particularly mammalian species, as "non-self" because of "self" tolerance. The term "tolerance" is well known in the art and refers to the failure of an animal's immune system to respond to its own tissues. To the animal's immune system, a highly conserved epitope appears to be "self", and no immune response is generated. Therefore, conventional animals are ineffective in the production of antibodies against such highly conserved epitopes.

There have been attempts in the prior art to address the problems found in the production of monoclonal antibodies, particularly with respect to the streamlining of the screening process for monoclonal antibodies and, to a certain extent, to the generation of a monoclonal antibody to an epitope that is highly conservative among animal species, particularly mammalian species.

One such attempt is described in U.S. Pat. No. 5,223,410 issued to Gargan et al. on Jun. 29, 1993, assigned to American Biogenetic Sciences, Inc. This patent describes a method for producing antibodies using an antigen-free animal. Particularly, it describes the production of monoclonal antibodies using sterile or germ-free mice. This patent focuses on the problem of streamlining of the screening processes for monoclonal antibodies by providing antigen-free or germ-free animals in which monoclonal antibodies can be more easily identified.

Korth et al. (1997) "Prion (PrPSc)-Specific Epitope Defined by a Monoclonal Antibody" (Letter to Nature) *Nature* 390:74 describes a monoclonal antibody, 15B3, that can discriminate between the normal and disease-specific forms of a prion (PrP). Prions are infectious particles causing transmissible spongiform encephalopathies. 15B3 specifically precipitates bovine, murine, or human PrPSc (the disease causing form), but not PrPc (the normal form), suggesting that it recognizes an epitope common to prions from different species. The 15B3 epitope was mapped as three polypeptide segments in PrP using immobilized synthetic peptides. However, the biological activity of this monoclonal antibody, which was produced from BALB/c mice, is uncharacterized.

In light of the above, a need exists for a method for making monoclonal antibodies against epitopes that are highly conservative among vertebrate, and particularly, mammalian species.

SUMMARY OF THE INVENTION

In accordance with the subject invention, a method is provided for the production of monoclonal antibodies to an antigen comprising:

(a) immunizing an animal having antibody-forming cells with disrupted peripheral tolerance with said antigen to permit said antibody-producing cells to produce antibodies to said antigen;

(b) removing at least a portion of said antibody-producing cells from said animal:

(c) forming a hybridoma by fusing one of said antibody-producing cells with an immortalizing cell wherein said hybridoma is capable of producing a monoclonal antibody to said antigen;

(d) propagating said hybridoma; and (e) harvesting the monoclonal antibodies produced by said hybridoma.

The subject invention also provides methods for utilizing a monoclonal antibody or a polyclonal antibody derived from an animal having antibody-forming cells with disrupted peripheral tolerance.

Alternatively, the present invention provides a process of detecting an antigen, wherein the process comprises immunoreacting the antigen with an antibody prepared according to the process described above to form an antibody-polypeptide conjugate, and detecting the conjugate.

In another aspect, the present invention contemplates a diagnostic assay kit for detecting the presence of an antigen in a biological sample, where the kit comprises a first container containing a first antibody capable of immunoreacting with antigen, with the first antibody present in an amount sufficient to perform at least one assay, and wherein the antibody is produced by the process described above. Preferably, an assay kit of the invention further comprises a second container containing a second antibody that immunoreacts with the first antibody, wherein the second antibody is produced by the processes described above. Thus, more preferably, the antibodies used in an assay kit of the present invention are monoclonal antibodies. Even more preferably, the first antibody is affixed to a solid support. More preferably still, the first and second antibodies comprise an indicator. Optionally, the indicator is a radioactive label or an enzyme.

In another embodiment, the present invention contemplates a diagnostic assay kit for detecting the presence, in a biological sample, of an antibody immunoreactive with an antigen, the kit comprising a first container containing the antigen that immunoreacts with the antibody, with the antigen present in an amount sufficient to perform at least one assay, and wherein the antibody is produced by the processes described above.

In another embodiment, the present invention contemplates a method of producing a non-human animal with an immune system having cells with a predetermined characteristic. The method comprises the steps of:

(a) obtaining an animal having immune system cells with a particular characteristic;

(b) obtaining another animal having immune system cells with either the same or a different characteristic from the animal of step (a); and (c) breeding the animal of step (a) with the animal of step (b) to produce an animal with an immune system having cells with a predetermined characteristic.

Accordingly, it is an object of this invention to provide an improved method for the production of antibodies, particularly monoclonal antibodies.

It is another object of this invention to provide a method for the production of antibodies, particularly monoclonal antibodies, using an animal having antibody producing cells with disrupted peripheral tolerance.

It is a further object of this invention to provide a method for the production of antibodies, particularly monoclonal antibodies, using an animal having antibody producing cells with disrupted peripheral tolerance.

It is still a further object of this invention to provide a method of producing a non-human animal with an immune system having cells with a predetermined characteristic.

Some of the aspects and objects of the invention having been stated hereinabove, other-aspects and objects will become evident as the description proceeds, when taken in

BRIEF DESCRIPTION OF THE DRAWINGS

FIGS. 3A–D depicts signal transduction through surface IgM and CD19 in B cells from (A)sHEL/Ig$^{HEL}$/hCD19$^{+/+}$ or (B) Ig$^{HEL}$/hCD19$^{+/+}$ mice. Relative [Ca$^{++}$]$_i$ levels were assessed by flow cytometry after gating on the B220$^+$ population of indo-1 loaded splenocytes. Baseline fluorescence ratios were collected for 1 min before HEL and/or specific monoclonal antibodies were added (arrows) at final concentrations of: HEL, 100 ng/ml; anti-mouse CD19, 40 µg/ml; anti-human CD19, 40 µg/ml. An increase in [Ca$^{++}$]$_i$ over time is shown as an increase in the ratio of indo-1 fluorescence. Values represent the ratios of fluorescence intensity of cell populations after treatment relative to the fluorescence intensity of untreated cells. These results are representative of those obtained from three littermate pairs of mice.

FIG. 5A depicts hybridoma supernatant fluid was assessed for reactivity with ssDNA by ELISA. Sera from autoimmune MRL$^{lpr/lpr}$ mice was used as a positive control. Values represent mean OD values (±SD) from triplicate wells. Similar results were obtained in three independent experiments.

FIG. 5B depicts reactivity of purified TG7-83 antibody with ssDNA compared with two established anti-ssDNA antibodies of the IgG1 isotype (452s.69 and 165s.3g). Reactivity was significantly higher (p<0.05, *p<0.01) than the negative control antibodies (B1-8 or TG18-161).

DETAILED DESCRIPTION OF THE INVENTION

Figure 1:
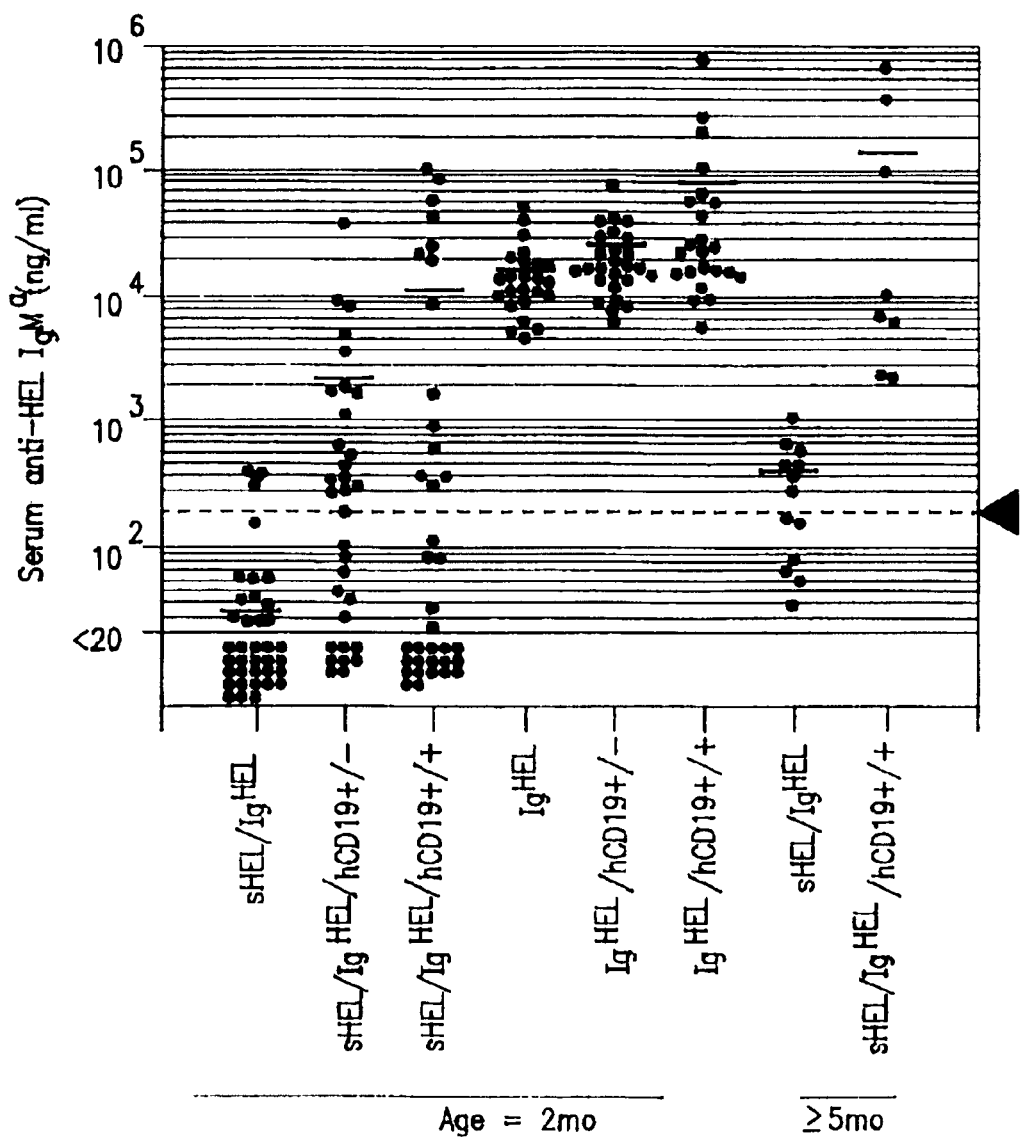
FIG. 1 depicts anti-HEL IgM$^a$ antibody levels in Ig$^{HEL}$ and sHEL/Ig$^{HEL}$ mice that overexpress CD19. Each value indicates serum levels of HEL-specific IgM$^a$ from individual 2-month-old (2 mo) or 5- to 10-month old (>5 mo) mice measured by ELISA. Horizontal bars indicating mean anti-HEL antibody concentrations for each group are provided for reference. The dashed horizontal line (arrowhead) delimits the 95% confidence interval for the log normal distribution of anti-HEL antibody levels observed in unimmunized 2-month-old sHEL/Ig$^{HEL}$ mice as described in Materials and Methods.

In the preferred embodiment of this invention transgenic mouse models for autoreactive B cells provide a mechanism for determining the role of CD19 signaling in regulating peripheral tolerance in autoimmunity. The CD19 cell surface molecule regulates signal transduction events critical for B lymphocyte development and humoral immunity. Increasing the density of CD19 expression renders B lymphocytes hyper-responsive to transmembrane signals, and transgenic mice that over-express CD19 have increased levels of autoantibodies. The role of CD19 in tolerance regulation and auto-antibody generation was therefore examined by crossing mice that overexpress a human CD19 transgene with transgenic mice expressing a model autoantigen (soluble hen egg lysozyme, sHEL) and high-affinity HEL-specific IgM$^a$ and IgD$^a$ (Ig$^{HEL}$ antigen receptors).

In the preferred model of peripheral tolerance, B cells in sHEL/Ig$^{HEL}$ double-transgenic mice are functionally anergic and do not produce autoantibodies. However, it was found that overexpression of CD19 in sHEL/Ig$^{HEL}$ double-transgenic mice resulted in a breakdown of peripheral tolerance and the production of anti-HEL antibodies at levels similar to those observed in Ig$^{HEL}$ mice lacking the sHEL autoantigen. Therefore, altered signaling thresholds due to CD19 overexpression resulted in the breakdown of peripheral tolerance. Thus, CD19 overexpression shifts the balance between tolerance and immunity to autoimmunity by augmenting antigen receptor signaling.

This surprising discovery indicates that animals having antibody producing cells with disrupted peripheral tolerance are useful in the production of monoclonal antibodies. Transgenic CD19 mice wherein CD19 is over-expressed experience a breakdown in peripheral tolerance. This renders B lymphocytes in such mice hyper-responsive to transmembrane signals. Such B lymphocytes are thus capable of distinguishing highly conserved epitopes in mammals when such epitopes are introduced to the mouse as an antigen. The immune system of a normal mouse would perceive such an epitope as identical to something that occurs naturally or is native to the mouse ("self"). In contrast, the immune system of the CD19 over-expressing transgenic mouse, and particularly the B lymphocytes of the mouse's immune system, recognize the highly conservative mammalian epitope as a particle foreign to the mouse's system ("non-self"), which would instigate an immune response.

This immune response is developed to produce monoclonal antibodies as described more fully herein. The demonstrated ability to break down peripheral tolerance as described herein and the breeding experiments described herein provide a method for manipulating the immune system of an animal such that an animal having an altered immune system with desired characteristics can be produced, as more fully described in Example 3.

While the following terms are believed to have well defined meanings in the art, the following definitions are set forth to facilitate explanation of the invention.

The term "immune system" includes all the cells, tissues, systems, structures and processes, including non-specific and specific categories, that provide a defense against "non-self" molecules, including potential pathogens, in an animal.

As is well known in the art, the non-specific immune system includes phagocytositic cells such as neutrophils, monocytes, tissue macrophages, Kupffer cells, alveolar macrophages and microglia. The specific immune system refers to the cells and other structures that impart specific immunity within a host. Included among these cells are the lymphocytes, particularly the B cell lymphocytes and the T cell lymphocytes. These cells also include natural killer (NK) cells. Additionally, antibody-producing cells, like B lymphocytes, and the antibodies produced by the antibody-producing cells are also included within the term "immune system".

The term "tolerance" is meant to refer to an animal's immune system's failure to respond to its own tissues or to tissues or molecules so like its own as to be recognized as its own.

The term "peripheral" or "peripheral lymphoid tissues" refer to the lymph node-, spleen-, or gut-associated lymphoid tissues wherein cells, such as B lymphocytes, of the immune system are developed.

Thus, the term "peripheral" in the context of the term "peripheral tolerance" indicates a tolerance, or failure to recognize an antigen, by a cell of the immune system, such as a B lymphocyte, in the peripheral lymphoid tissues wherein such cells usually react with antigens.

The term "disrupted peripheral tolerance", as used herein and in the claims, means any manipulation or alteration of the peripheral tolerance of the antibody-producing cells of the immune system. Preferably, the term "disrupted peripheral tolerance" is meant to refer to the break down of peripheral tolerance, which facilities monoclonal antibody production in accordance with the methods of the present invention.

The term "anergy" means a condition in which the immune system of an animal fails to respond to the injection of an antigen. Thus, the term "peripheral anergy" means a condition in which the peripheral immune system of an animal fails to respond to the injection of an antigen.

The term "autoantibody" means an antibody formed against an epitope native to the animal.

The term "antibody-producing cell" refers to any antibody-producing cell within the immune system. Preferably, it is meant to refer to B lymphocytes.

The term "complement" is meant to refer to the non-specific defense system that is activated by the bonding of antibodies to antigens and by this means is directed against specific invaders that have been identified by antibodies. Eleven complement proteins have been characterized in the field and are generally referred to by those having ordinary skill in the art as C1–C9. The complement proteins act generally along a cascade wherein they contribute to (1) recognition (C1); (2) activation (C4, C2, and C3, in that order); and (3) attack (C5–C9). During the attack phase, complement proteins attach to the cell membrane and destroy the victim cell in a process known as complement fixation. The complement system is well known in the art and is more fully described in Fox, *Human Physiology*, William C. Brown Pub., DuBuque, Iowa (1987).

The term "humoral immunity" is meant to refer to the form of acquired immunity in which antibody molecules are secreted in response to antigenic stimulation.

The term "cell-mediated immunity" is meant to refer to the immunological defense provided by T cell lymphocytes, which come into close proximity to their victim cells.

The terms "B cell lymphocytes" or "B lymphocytes" are meant to refer to a type of lymphocyte that can be transformed by antigens into plasma cells that secrete antibodies, and are thus responsible for humoral immunity.

The term "T cell lymphocytes" is meant to refer to a type of lymphocyte that provides cell-mediated immunity, in contrast to B lymphocytes that provide humoral immunity to the secretion of antibodies. There are three sub-populations of T cells: cytotoxic, helper, and suppressor.

The terms "overexpress", "overexpressing" and "overexpressed" refer to any level of expression of a gene or protein, whether the gene be a transgene or a normal gene, that exceeds normal or expected levels of expression by any amount.

Following long-standing patent law convention, the terms "a" and "an" mean "one or more" when used in this application, including the claims.

In the following Detailed Description, the use of transgenic mice which overexpress CD19 is described as a preferred embodiment of the instant invention. Such transgenic mice have been developed in the field according to published techniques (see, for example, Engel et al. (1995) *Immunity* 3:39–50 and Zhou (1994) *Mol. Cell. Biol.* 14:3884–3894). Thus, these mice are conveniently available as starting materials. However, it also should be noted that there has been no disclosure of the production of monoclonal antibodies until the instant disclosure.

Given advances in transgenic animal techniques, which have been published in the art, it is believed that any animal can be utilized in the subject invention, including mouse, pig, rat, rabbit, guinea pig, goat, sheep, primate, and poultry.

Moreover, while CD19 overexpressing transgenic mice are preferred because the break down in peripheral tolerance of antibody-producing cells found in these mice, other animals having a manipulated or altered characteristics in the cells of their immune system are contemplated to be within the scope of this invention. Moderate levels of disrupted peripheral tolerance have been described in the art with respect to the manipulation of CD45 and with respect to the manipulation of LPR mice. But, there has been no disclosure of the production of monoclonal antibodies until the instant disclosure. Finally, other particular candidate characteristics for manipulation are provided in Example 3.

Production of Monoclonal Antibodies

The animal having antibody-forming cells with disrupted peripheral tolerance is utilized for the production of monoclonal antibodies. The system can be utilized to produce a monoclonal antibody to any antigen that the animal not having antibody-forming cells with disrupted peripheral tolerance could produce. An exemplary list of antigens appears in U.S. Pat. No. 3,935,074, the contents of which are herein incorporated by reference.

However, the animal having antibody-forming cells, such as B lymphocytes, with disrupted peripheral tolerance provides a much enhanced immune response to the antigen. Thus, one can increase the likelihood of locating a B-lymphocyte that produces an antibody that is capable of binding to a specific epitope of the antigen. This is a major advantage of the subject invention. In addition, the system having antibody-forming cells with disrupted peripheral tolerance system is particularly useful for generating a highly specific antibody for those antigens with numerous epitopes.

Preferably, the system having antibody-forming cells with disrupted peripheral tolerance is used to generate monoclonal antibodies to epitopes that are highly conserved among vertebrate and particularly, mammalian species. Animals not having antibody-forming cells with disrupted peripheral tolerance do not typically respond to such highly conserved epitopes because of self-tolerance. Stated differently, the immune systems of conventional animals cannot recognize highly conserved epitopes as "non-self" and therefore cannot produce antibodies against such an epitope. The immune systems of the animals of the instant invention, can recognize highly conserved epitopes as "non-self" because of the antibody-forming cells with disrupted peripheral tolerance.

The animals of the instant invention can be immunized by standard techniques. For example, the animal be immunized at least two times with at least about three weeks between each immunization, followed by a prefusion booster.

Somatic Cells

Somatic cells of the animal having the potential for producing antibody and, in particular B lymphocytes, are suitable for fusion with a B-cell myeloma line. Those antibody-producing cells that are in the dividing plasmablast stage fuse preferentially. Somatic cells can be derived from the lymph nodes, spleens and peripheral blood of primed animals, and the lymphatic cells of choice depend to a large extent on their empirical usefulness in the particular fusion system. However, somatic cells derived from the spleen are generally preferred. Once primed or hyperimmunized, animals having antibody-forming cells with disrupted peripheral tolerance can be used as a source of antibody-producing lymphocytes. Mouse lymphocytes give a higher percentage of stable fusions with the mouse myeloma lines described herein below. Indeed, mice are the preferred animals for use in making monoclonal antibodies because of the availability of excellent cell lines to use as fusion partners. However, the use of antibody-producing cells from other animals is also possible. The choice of a particular animal depends on the choice of antigen, for it is important that the animal have a B-lymphocyte in its repertoire of B-lymphocytes that can produce an antibody to such antigen.

Immortalizing Cells

Specialized myeloma cell lines have been developed from lymphocyte tumors for use in hybridoma-producing fusion procedures (G. Kohler and C. Milstein (1976) *Eur. J. Immunol.* 6:511–519; M. Schulman et al. (1978) *Nature* 276:269–270). The cell lines have been developed for at least three reasons. The first reason is to facilitate the selection of fused myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is their suitability and efficiency for fusion.

Several myeloma cell lines can be used for the production of fused cell hybrids, including NS-1, X63-Ag8, NIS-Ag4/1, MPC11-45.6TG1.7, X63-Ag8.653, Sp2/O-Agf14, FO, and S194/5XXO.Bu.1., all derived from mice, and 210-.RCY3.Agl.+B2.3+L derived from rats. (G. J. Hammerling, U. Hammerling and J. F. Kearnly, eds. (1981), *Monoclonal antibodies and hybridomas*, J. L. Turk, eds. *Research Monographs in Immunology*, Vol. 3, Elsevier/North Holland Biomedical Press, New York).

Fusion

Methods for generating hybrids of antibody-producing spleen or lymph node cells and immortalizing cells generally comprise mixing somatic cells with immortalizing cells in a proportion which can vary from about 20:1 to about 1:1 in the presence of an agent or agents (chemical, viral or electrical) that promote the fusion of cell membranes. It is often preferred that the same species of animal serve as the source of the somatic and immortalizing cells used in the fusion procedure. Fusion methods have been described by Kohler and Milstein (1975), *Nature* 256:495–497; (1976), *Eur. J. Immunol.* 6:511–519; by Gefter et al. (1977), *Somatic Cell Genet* 3:231–236 and by Kozbor et al. (1983), *Immunology Today*, 4:72. The fusion-promoting agents used by those investigators were Sendai virus and polyethylene glycol (PEG), respectively.

One can also utilize the recently developed EBV-transformation technique (Cole et al. (1985), *Monoclonal Antibodies and Cancer Therapy*, Alan R. Liss, Inc., pp. 77–96).

Isolation of Clones and Antibody Detection

Fusion procedures usually produce viable hybrids at very low frequency, about $1\times10^{-5}$ to $1\times10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium, which contains hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells can synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B-lymphocytes is diluted in HAT medium and cultured in multiple wells of microtiter plates. In two to three weeks, when hybrid clones become visible microscopically, the supernatant fluid of the individual wells containing hybrid clones is assayed for specific antibody production.

The assay must be sensitive, simple and rapid. Assay techniques include radioimmunoassays, enzyme immunoassays, cytotoxicity assays, and plaque assays.

Cell Propagation and Antibody Production

Once the desired fused cell hybrids have been selected and cloned into individual antibody-producing cell lines, each cell line can be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines can be propagated in vitro in laboratory culture vessels. The culture medium, containing high concentrations of a single specific monoclonal antibody, can be harvested by decantation, filtration or centrifugation.

Use of the Monoclonal Antibody

The monoclonal antibodies made by the method of the subject invention can be utilized in any technique known or to be developed in the future that utilizes a monoclonal antibody.

A major use of monoclonal antibodies is in an immunoassay, which is the measurement of the antigen-antibody interaction. Such assays are generally heterogeneous or homogeneous. In a homogeneous immunoassay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth. The major advantage of a homogeneous immunoassay is that the specific antibody need not be separated from the labeled analyte.

In a heterogeneous immunoassay, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescers, enzymes, and so forth. Exemplary of heterogeneous immunoassays are the radioimmunossay, immunofluoroescence methods, enzyme-linked immunoassays, and the like.

For a more detailed discussion of the above immunoassay techniques, see *Enzyme-Immunoassay*, by Edward T. Maggio, CRC Press, Inc., Boca Raton, Fla., (1980). See also, for example, U.S. Pat. Nos. 3,690,834; 3,791,932; 3,817, 837; 3,850,578; 3,853,987; 3,867,517; 3,901,654; 3,935, 074; 3,984,533; 3,996,345; and 4,098,876, the contents of each of which are herein incorporated by reference, and which listing is not intended to be exhaustive.

Another major use of monoclonal antibodies are in vivo imaging and therapeutics. The monoclonal antibodies can be labeled with radioactive compounds, for instance, radioactive iodine, and administered to a patient intravenously. The antibody can also be labeled with a magnetic probe. NMR can then be utilized to pinpoint the antigen. After localization of the antibodies at the antigen, the antigen can be detected by emission tomographical and radionuclear scanning techniques, thereby pinpointing the location of the antigen.

By way of illustration, the purified monoclonal antibody is suspended in an appropriate carrier, e.g., saline, with or without human albumin, at an appropriate dosage and is administered intravenously, e.g., by continuous intravenous infusion over several hours, as in Miller et al., *In Hybridomas in Cancer Diagnosis and Therapy* (1982), incorporated herein by reference.

The monoclonal antibodies of subject invention can be used therapeutically. Antibodies with the proper biological properties are useful directly as therapeutic agents. Alternatively, the antibodies can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68:317–328).

It also is believed that polyclonal antibodies derived from an animal having antibody-producing cells with disrupted peripheral tolerance also can be utilized in immunoassays and provide an improved result as compared to polyclonal antibodies derived from a conventional animal. Polyclonal antibodies derived from an animal having antibody-producing cells with disrupted peripheral tolerance can be made by utilizing such an animal, as described hereinabove, and immunization techniques, as described hereinabove, followed by separating the polyclonal antibodies from the animal by conventional techniques, e.g. by separating the serum from the animal.

Means for preparing and characterizing antibodies are well known in the art (See, e.g., *Antibodies-A Laboratory Manual*, E. Howell and D. Lane, Cold Spring Harbor Laboratory, 1988). Monoclonal antibodies can be readily prepared through use of well-known techniques such as those exemplified in U.S. Pat. No 4,196,265, herein incorporated by reference.

Pharmaceutical Compositions

In a preferred embodiment, the present invention provides pharmaceutical compositions comprising a monoclonal antibody produced by a process of the present invention and a physiologically acceptable carrier. Such a composition has a variety of uses, including, for example but not limited to, use as a delivery agent for a cytotoxic substance as described herein.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like.

Assay Kits

In another aspect, the present invention contemplates diagnostic assay kits for detecting the presence of an antigen in biological samples, where the kits comprise a first container containing a first antibody capable of immunoreacting with the antigen with the first antibody present in an amount sufficient to perform at least one assay, the antibody obtained from an animal having antibody-producing cells with disrupted peripheral tolerance. Preferably, the assay kits of the invention further comprise a second container containing a second antibody that immunoreacts with the first antibody, the second antibody obtained from an animal having antibody-producing cells with disrupted peripheral tolerance. Thus more preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The following Examples have been included to illustrate preferred modes of the invention. Certain aspects of the following Examples are described in terms of techniques and procedures found or contemplated by the present inventor to work well in the practice of the invention. These Examples are exemplified through the use of standard laboratory practices of the inventor. In light of the present disclosure and the general level of skill in the art, those of skill will appreciate that the following Examples are intended to be exemplary only and that numerous changes, modifications and alterations can be employed without departing from the spirit and scope of the invention.

EXAMPLE 1

CD19-Regulated Signaling Thresholds Control Peripheral Tolerance and Autoantibody Production in B Lymphocytes B lymphocyte tolerance to self antigens is achieved by the negative selection and elimination of immature B cells that express high-affinity IgM receptors for autoantigens. Goodnow, C. C. (1996) *Proc. Natl. Acad. Sci. USA* 93:2264–2271; Hartley et al. (1993) *Cell* 72:325–335; Nemazee et al. (1989) *Nature* 337:562–566; Goodnow, C. C. (1992) *Annu. Rev. Immunol.* 10:489–518. Negative selection is antigen receptor-dependent but also relies on established triggering thresholds for intracellular signals (Goodnow, C. C. (1996) *Proc. Natl. Acad, Sci. USA* 93:2264–2271; Klinman, N. R. (1996) *Immunity* 5:189–195). If antigen receptor ligation generates inadequate intracellular signals because of a low affinity for autoantigens, or the valency or concentration of autoantigen is low, autoreactive B cells mature and leave the bone marrow but are rendered functionally anergic. Goodnow, C. C. (1996) *Proc. Natl. Acad. Sci. USA* 93:2264–2271; Goodnow, C. C. (1992) *Annu. Rev. Immunol.* 10:489–518; Klinman, N. R. (1996) *Immunity* 5:189–195; Adelstein et al. (1991) *Science* 251:1223–1225; Nemazee et al. (1991) *Immunol. Rev.* 122:117–132. Intracellular signaling thresholds are likely to also play a major role in the regulation and maintenance of peripheral tolerance.

The CD19 cell surface molecule regulates intracellular signaling thresholds critical for B cell development and humoral immunity. Tedder et al. (1997) *Immunity* 6:107–118; Fearon et al. (1996) *Science* 272:50–54; Carter et al. (1992) *Science* 256:105–107; Dempsey et al. (1996) *Science* 271:348–350; Engel et al. (1995) *Immunity* 3:39–50; Rickert et al. (1995) *Nature* 376:352–355. B lymphocytes from mice that overexpress CD19 are hyper-responsive to antigen receptor crosslinking, which results in serum immunoglobulin (Ig) levels that are increased by about 40% and humoral responses that are augmented several fold. Engel et al. (1995) *Immunity* 3:39–50; Sato et al. (1995) *Proc. Natl. Acad. Sci. USA* 92:11558–11562; Zhou et al. (1994) *Mol. Cell. Biol.* 14:3884–3894. Based on this, it was expected that CD19 overexpression by autoreactive B cells would either lead to their augmented negative selection in the bone marrow or result in a more profound state of peripheral anergy.

Unexpectedly however, C57BL/6 mice that overexpress CD19 have twofold to fourfold higher levels of anti-DNA autoantibodies and rheumatoid factor. Tedder et al. (1997) *Immunity* 6:107–118; Sato et al. (1996) *J. Immunol.* 156:4371–4378. Increased autoantibody production in mice overexpressing CD19 correlates with dramatic increases in the number of B1 lineage cells. However, since IgG anti-DNA autoantibodies are preferentially increased in mice that overexpress CD19, the CD19-induced autoantibodies may alternatively result from alterations in conventional B-cell tolerance.

Transgenic mouse models for autoreactive B cells (Goodnow, C. C. (1992) *Annu. Rev. Immunol.* 10:489–518; Nemazee et al. (1991) *Immunol. Rev.* 122:117–132) provide a mechanism for determining the role of CD19 signaling in regulating peripheral tolerance and autoimmunity. B cells from transgenic mice expressing a model autoantigen (soluble hen egg lysozyme, sHEL) and high-affinity HEL-specific IgM$^a$ and IgD$^a$ (Ig$^{HEL}$) antigen receptors enter the peripheral pool but are anergic to antigen receptor ligation and produce little, if any, spontaneous HEL-specific antibody. Goodnow et al. (1988) *Nature* 334:676–682. Mice that express a human CD19 (hCD19) transgene provide a model for examining augmented CD19 function in vivo. Tedder et al. (1997) *Immunity* 6:107–118; Sato et al. (1995) *Proc. Natl. Acad. Sci. USA* 92:11558–11562; Zhou et al. (1994) *Mol. Cell. Biol.* 14:3884–3894; Sato et al. (1996) *J. Immunol.* 156:4371–4378; Sato et al. (1997) *J. Immunol.* 158:4662–4669) Since hCD19 can replace the function of mouse CD19 in vivo, hemizygous hCD19$^{+/-}$ transgenic mice express cell surface CD19 at a twofold higher density while hCD19$^{+/+}$ transgenic mice express threefold higher densities of CD19. Sato et al. (1996) *J. Immunol.* 156:4371–4378; Sato et al. (1997) *J. Immunol* 158:4662–4669.

Therefore, sHEL/Ig$^{HEL}$ double-transgenic mice were crossed with hCD19 transgenic mice to determine whether tolerance would be maintained in sHEL/Ig$^{HEL}$/hCD19 transgenic mice or autoantibodies would be generated. CD19 overexpression in sHEL/Ig$^{HEL}$ double-transgenic mice resulted in the production of anti-HEL antibodies at levels similar to those observed in Ig$^{HEL}$ mice lacking this model self antigen. Therefore, lowered signaling thresholds due to CD19 overexpression resulted in the breakdown of peripheral tolerance in sHEL/Ig$^{HEL}$ double-transgenic mice.

Mice. hCD19 transgenic mice (h19-1 line, C57BL/6) were produced as described in Engel et al. (1995) *Immunity* 3:39–50 and in Zhou et al. (1994) *Mol. Cell. Biol.* 14:3884–3894). In the h19-1 line of mice, 9–14 copies of the hCD19 transgene are integrated into a single (or closely linked) site(s). These h19-1 mice used in this study were backcrossed onto a wild-type C57BL/6 background for 8 to 10 generations without a diminution of hCD19 expression and all mice express similar levels of cell-surface hCD19. Mice expressing sHEL (ML5 line)and Ig$^{HEL}$ (MD4 line) were as described (Goodnow et al. (1988) *Nature* 334:676–682; Hartley et al. (1991) *Nature* 353:765–769). sHEL/Ig$^{HEL}$/hCD19 triple-transgenic mice were generated by appropriate backcrosses of sHEL/Ig$^{HEL}$ double-transgenic mice with hCD19$^{+/+}$ mice. Transgene expression was assessed as described in (Engel et al. (1995) *Immunity* 3:39–50; Zhou et al. (1994) *Mol. Cell. Biol.* 14:3884–3894; Goodnow et al. (1988) *Nature* 334:676–682; Hartley et al. (1991) *Nature* 353:765–769.) Mice were housed in a specific pathogen-free barrier facility. All studies and procedures were approved by the Duke University Animal Care and Use Committee.

Immunization of Mice. Two-month-old mice were immunized i.p. with 100 μg of HEL in complete Freund's adjuvant (CFA, Sigma Chemical Co.) or PBS in CFA at day 0 and were boosted at day 21. Animals were bled just before the first immunization and 7, 14, and 28 days later.

Mouse Ig Isotype-specific ELISAs. Serum levels of HEL-specific IgM allotype a (IgM$^a$) antibody were measured by ELISA on HEL-coated plates as described (Goodnow et al. (1989) Nature 342:385–391). Absolute antibody concentrations were determined relative to a standard curve of HEL-specific IgM$^a$ monoclonal antibody (E1 clone) generated from an IgHEL transgenic mouse immunized with HEL. The ELISA sensitivity limit was about 20 ng/ml of anti-HEL IgM$^a$ antibody.

Immunofluorescence Analysis. Antibodies used in this study included: FITC-conjugated and biotin-coupled goat anti-mouse IgM isotype-specific antibodies (Southern Biotechnology Associates, Inc., Birmingham, Ala.); anti-B220 (CD45RA, RA3-6B2, provided by R. L. Coffman, DNAX Research Inst., Palo Alto, Calif.), anti-I-A (M5/114.15.2, American Type Culture Collection (ATCC), Bethesda, Md., clone TIB120), anti-HSA (M1/69, PharMingen, San Diego, Calif.), anti-CD5 (53-7.313, ATCC, clone TIB104), anti-B7-2 (GL-1, PharMingen) and anti-mouse IgM$^a$ (DS-1, PharMingen) monoclonal antibodies. Phycoerythrin-conjugated streptavidin (Fisher Scientific, Fair Lawn, N.J.) was used to reveal biotin-coupled monoclonal antibody staining. Phycoerythrin-conjugated goat anti-rat IgG antibodies (Caltag, Burlingame, Calif.) were used to visualize anti-CD5 monoclonal antibody staining. Cells reacting with biotin-coupled HEL were stained with phycoerythrin-conjugated streptavidin. Isolated lymphocytes were analyzed on a FACScan® flow cytometer (Becton-Dickinson, San Jose, Calif.) as described (Sato et al. (1996) J. Immunol. 156:4371–4378.)

Measurement of Intracellular Calcium. Splenocytes were isolated, loaded with indo-1 and stained with FITC-labeled anti-B220 antibodies as described (Sato et al. (1996) Immunity 5:551–562.). Relative intracellular Ca$^{++}$ levels ([Ca$^{++}$]$_i$) were assessed by flow cytometry after gating on the B220$^+$ population of cells. Baseline fluorescence ratios were collected for 1 min before HEL and/or specific monoclonal antibodies were added at final concentrations of: HEL, 100 ng/ml; anti-mouse CD19, 40 μg/ml (MB19-1, IgA) (Sato et al. (1996) J. Immunol. 156:4371–4378); and anti-human CD19, 40 μg/ml (HB12b, IgG1) (Bradbury et al. (1992) J. Immunol. 149:2841–2850.) An increase in the ratio of indo-1 fluorescence indicates an increase in [Ca$^{++}$]$_i$.

Statistical Analysis. All data are shown as mean values±SEM. Analysis of variance (ANOVA) was used to analyze the data, and the Student's t test was used to compare population sample means. The Mann-Whitney test was also used to compare population frequency distributions. The 95% confidence interval for anti-HEL antibody levels observed in sHEL/Ig$^{HEL}$ mice was determined using the log normal distribution (mean±2 SD) of antibody values with undetectable levels (<20 ng/ml) assigned the value of 10 ng/ml.

Autoantibodies in sHEL/Ig$^{HEL}$/hCD19 transgenic mice. Serum anti-HEL IgM$^a$ autoantibody levels in Ig$^{HEL}$ transgenic, sHEL/Ig$^{HEL}$ double-transgenic, and sHEL/Ig$^{HEL}$/hCD19 triple-transgenic mice were determined to assess the status of B cell tolerance in each set of mice. Serum antibody levels for each individual mouse are shown in FIG. 1 and mean autoantibody levels for each set of mice are provided to simplify discussion of the results. Two-month-old sHEL/Ig$^{HEL}$ double transgenic mice produced very low or undetectable levels of anti-HEL IgM$^a$ antibodies (mean levels 31 ng/ml) when compared with Ig$^{HEL}$ transgenic mice (mean 16,700 ng/ml, FIG. 1). However, 45% (14 of 33) of sHEL/Ig$^{HEL}$/hCD19$^{+/-}$ mice had anti-HEL IgM$^a$ autoantibody levels (mean 2,430 ng/ml) that were significantly greater than those found in sHEL/Ig$^{HEL}$ mice (P≦0.001, FIG. 1). Anti-HEL IgM$^a$ antibody levels were also elevated in 38% (14 of 36) of sHEL/Ig$^{HEL}$/hCD19$^{+/+}$ mice (mean 10,500 ng/ml, P≦0.01, FIG. 1). Autoantibody levels in some sHEL/Ig$^{HEL}$/hCD19 mice were equivalent to those of Ig$^{HEL}$-transgenic mice not expressing sHEL. In fact, overexpression of CD19 resulted in anti-HEL autoantibody levels in some mice that were one thousand (1,000)-fold higher than in sHEL/Ig$^{HEL}$ mice. By comparison, overexpression of CD19 in Ig$^{HEL}$/CD19$^{+/+}$ mice resulted in only a fourfold increase in anti-HEL antibody levels (mean 77,300 ng/ml, FIG. 1). Thus, lowered signaling thresholds resulting from the overexpression of CD19 abrogated peripheral anergy in a significant proportion of two-month-old sHEL/Ig$^{HEL}$ mice.

The breakdown in peripheral tolerance and the development of autoantibodies in sHEL/Ig$^{HEL}$ mice that overexpressed CD19 correlated with mouse age. By five to ten months of age, all sHEL/Ig$^{HEL}$/hCD19$^{+/+}$ mice produced significantly higher levels of autoantibodies (mean 144,000 ng/ml) than sHEL/Ig$^{HEL}$ mice (300 ng/ml, P<0.01, FIG. 1). The lowest autoantibody level found in a five-month-old sHEL/Ig$^{HEL}$/hCD19$^{+/+}$ mouse was 2,300 ng/ml. Therefore, the breakdown of tolerance in sHEL/Ig$^{HEL}$/hCD19$^{+/+}$ mice had 100% penetrance by five months of age.

Figure 2A:
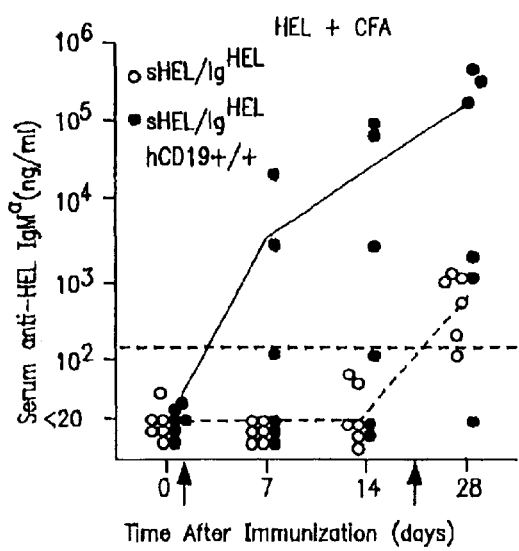
FIGS. 2A–D depicts humoral immune responses of (A) sHEL/Ig$^{HEL}$ and (B) Ig$^{HEL}$ mice that overexpress CD19 in response to immunization with HEL. Two-month-old mice were injected i.p. with HEL or PBS mixed with CFA on days 0 and 21 (arrows), and were bled at the indicated times. Levels of serum anti-HEL IgM$^a$ antibodies for individual mice (dots or squares) were determined by ELISA. Mean antibody levels are shown as solid (hCD19$^{+/+}$) or dashed (hCD19$^{-/-}$) lines. The dashed horizontal lines (arrowhead) delimit the 95% confidence interval for the log normal distribution of anti-HEL antibody levels observed in unimmunized sHEL/Ig$^{HEL}$ mice.
Figure 2B:
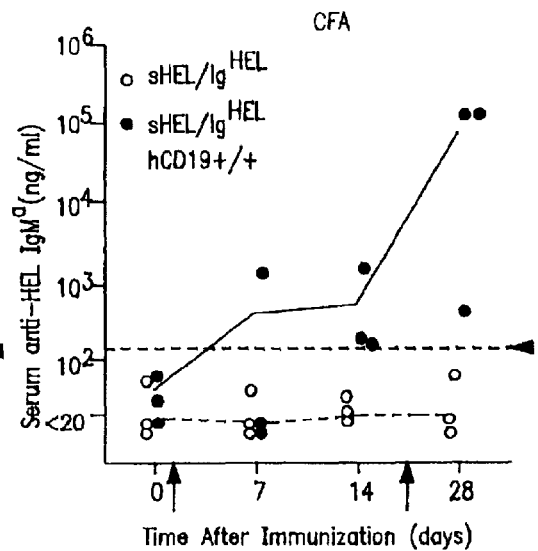
Figure 2C:
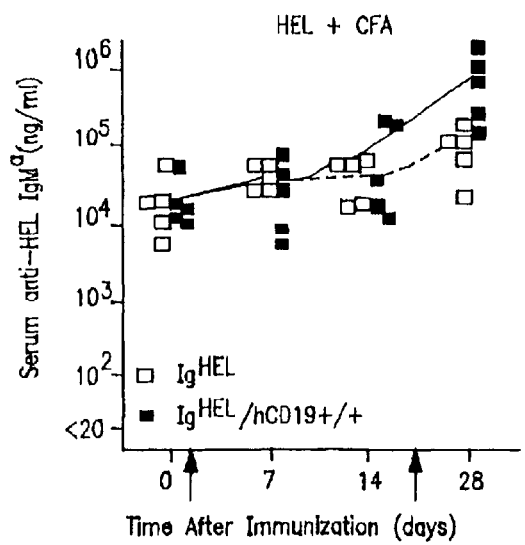
Figure 2D:
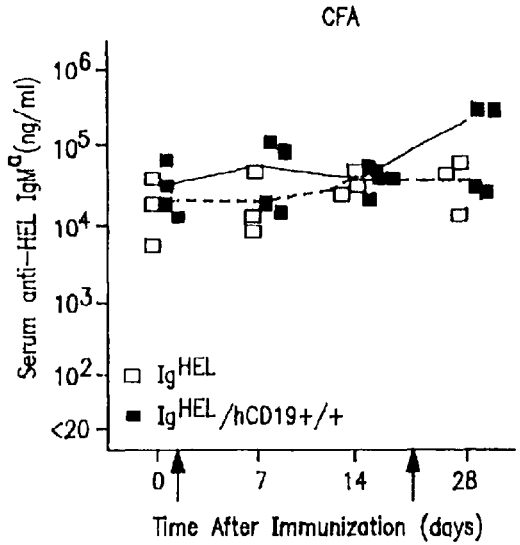

Abrogation of peripheral tolerance in sHEL/Ig$^{HEL}$/hCD19 mice. Whether B-cell anergy could be surmounted in young mice that overexpress CD19 was assessed by immunizing two-month-old mice with HEL in CFA. Mice without detectable levels of spontaneous anti-HEL antibodies were also injected with CFA alone to mimic a nonspecific inflammatory stimulus. Immunization of sHEL/Ig$^{HEL}$/hCD19$^{+/+}$ mice with HEL generated primary anti-HEL antibody responses in some mice, and a mean secondary antibody response that was two hundred-fold higher (P<0.05) than that of sHEL/Ig$^{HEL}$ mice (FIG. 2A). A measurable antibody response was only detected in sHEL/Ig$^{HEL}$ mice after secondary immunization (FIG. 2A). A striking result was that the inflammation induced by CFA alone induced sHEL/Ig$^{HEL}$/hCD19$^{+/+}$ mice to produce anti-HEL antibodies in response to endogenous sHEL autoantigen (FIG. 2A). In this case, the mean secondary antibody response was 4 thousandfold higher than in sHEL/Ig$^{HEL}$ mice (P<0.05). In fact, the anti-HEL antibody levels induced in some sHEL/Ig$^{HEL}$/hCD19$^{+/+}$ mice were equivalent to those of Ig$^{HEL}$ mice (FIG. 2B). Similar results were obtained with sHEL/Ig$^{HEL}$/hCD19$^{+/-}$ mice although anti-HEL autoantibody levels were intermediate. In sHEL/Ig$^{HEL}$/hCD19$^{+/+}$ mice that already expressed detectable anti-HEL antibodies, autoantibody levels were also dramatically augmented following CFA administration. Therefore, inflammatory responses induced by the administration of CFA revealed a breakdown in tolerance and resulted in autoantibody production in anergic mice that overexpressed CD19.

Effects of CD19 overexpression on B-cell development. The effects of CD19 overexpression on B-cell development was assessed to elucidate the cellular basis for the breakdown of peripheral tolerance in sHEL/Ig$^{HEL}$ mice. The breakdown in tolerance did not result from relaxed negative selection, since the number of mature IgM$^+$B220$^{hi}$ or HSA$^{lo}$ B220$^{hi}$ B cells in the bone marrow, blood, and spleen of Ig$^{HEL}$/hCD19$^{+/+}$ mice was significantly reduced in the absence or presence of sHEL (Table 1).

B cell development in Ig$^{HEL}$ and sHEL/Ig$^{HEL}$ mice that overexpress CD19 was analyzed using flow cytometry. The results are discussed herein below. Representative two-color immunofluorescence staining of B cells from A) bone marrow, B) blood, C) spleens, and D) peritoneum of littermate pairs was performed. B lymphocytes were revealed by B220 or IgM expression. Quadrants delineated by squares indicated the pre-B cell (B220$^{lo}$IgM$^-$), immature B cell (B220$^{lo}$IgM$^+$) and mature B cell (B220$^{hi}$IgM$^+$) compartments, with numbers representing the percentage of cells within quadrants. The gates that defined mature B lymphocytes for sHEL/Ig$^{HEL}$ mice were different from the gate used for IgHEL mice since surface IgM levels are downregulated in sHEL/Ig$^{HEL}$ mice. Spleen cells were also stained for B220 or IgM and counterstained for sHEL binding or I-A expression.

Additional gates were used to determine the frequency of the CD5$^+$B220$^+$ population and CD5$^-$B220$^+$ population of cells for Table 1. Populations of cells lacking surface antigen expression were determined using unreactive monoclonal antibodies as controls. All samples were stained in parallel and analyzed sequentially by flow cytometry with identical instrument settings. Relative fluorescence intensity was shown on a four decade log scale, with 50% log density contour levels. Horizontal dashed lines in some histograms were provided for reference. Similar results were obtained with at least five sets of mice. Equivalent results were obtained by using anti-IgM$^a$ antibody instead of anti-IgM antibody.

A similar decrease in the generation of mature B cells occurs, presumably as a consequence of increased clonal elimination, in wild-type mice that overexpress CD19. Zhou et al. (1994) Mol. Cell. Biol. 14:3884–3894. However, since all B cells bear the same receptor with the same affinity for antigen, the partial decrease in generation of mature B cells in the bone marrow of Ig$^{HEL}$/hCD19$^{+/+}$ mice and sHEL/Ig$^{HEL}$/hCD19$^{+/+}$ mice suggests that this developmental bottleneck occurs independent of antigen receptor ligation. Further, it is difficult to imagine a deleting antigen that binds to the transgenic receptor better than HEL, and deletion also occurs in mice lacking sHEL. Therefore, overexpression of CD19 may alter the generation of mature B cells through mechanisms in addition to increased negative selection. Nonetheless, the breakdown in tolerance did not result from relaxed negative selection.

Peripheral B cell numbers were significantly reduced in both Ig$^{HEL}$ mice and sHEL/Ig$^{HEL}$ mice overexpressing CD19 (Table 1). Overexpression of CD19 reduced circulating B cell numbers by 87% in Ig$^{HEL}$ mice and 78% in sHEL/Ig$^{HEL}$ mice. CD19 overexpression reduced spleen B cell numbers by 42% in Ig$^{HEL}$ mice and 48% in sHEL/Ig$^{HEL}$ mice. Conventional B cells within the peritoneum were also reduced by >90% in Ig$^{HEL}$/hCD19$^{+/+}$ and sHEL/Ig$^{HEL}$/hCD19$^{+/+}$ mice. Overexpression of CD19 did not induce the generation of B cells with the phenotypic characteristics of either B1a or B1b cells and only small numbers of CD5$^+$ B220$^{lo}$ B cells were observed in any of the 2-month-old transgenic mouse lines (Table 1). In addition, all of the HEL-binding B cells in each line of mice were conventional B cells since they were CD5$^-$, CD23$^+$, IgD$^{hi}$, and B220$^{hi}$. Thus, the dramatic increase in the levels of autoantibodies generated in sHEL/Ig$^{HEL}$/hCD19$^{+/+}$-transgenic mice were even more significant given the >50% reduction in numbers of peripheral B cells in these mice.

Chronic stimulation through the B-cell antigen receptor in sHEL/Ig$^{HEL}$ mice results in a unique IgM$^{lo}$IgD$^{hi}$ phenotype with increased expression of class II (I-A) antigens (Goodnow et al. (1988) Nature 334:676–682; Goodnow et al. (1989) Nature 342:385–391; Mason et al. (1992) Intl. Immunol. 4:163–175). In comparison, the overexpression of hCD19$^{+/+}$ in these mice resulted in even lower IgM expression and higher I-A expression (Table 1). Despite the decrease in surface IgM, all B cells from sHEL/Ig$^{HEL}$/hCD19$^{+/+}$ mice still bound sHEL in vitro in proportion to their IgM$^a$ density. B cells from Ig$^{HEL}$/hCD19$^{+/+}$ transgenic mice had an intermediate gM$^{lo}$I-A$^{hi}$ phenotype even in the absence of sHEL (Table 1). B cells from mice that overexpressed CD19 also expressed significantly elevated levels of cell surface CD86 (B7-2). Therefore, CD19 overexpression appeared to augment the phenotypic outcome of signaling through the B cell antigen receptor in the absence or presence of autoantigen. However, B cells from sHEL/Ig$^{HEL}$/hCD19$^{+/+}$ mice still exhibited a phenotype that is characteristic of anergic B cells.

Figure 3B:
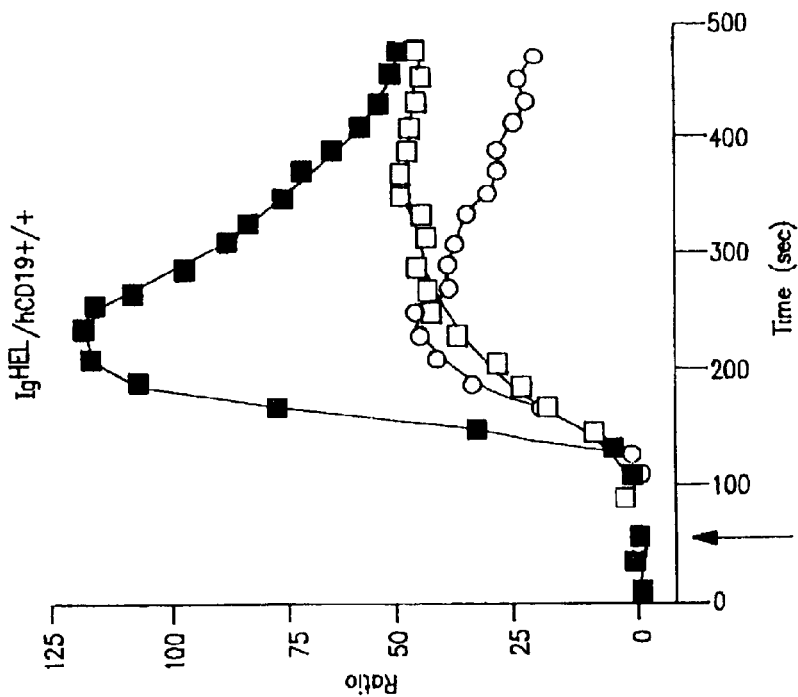
Figure 3A:
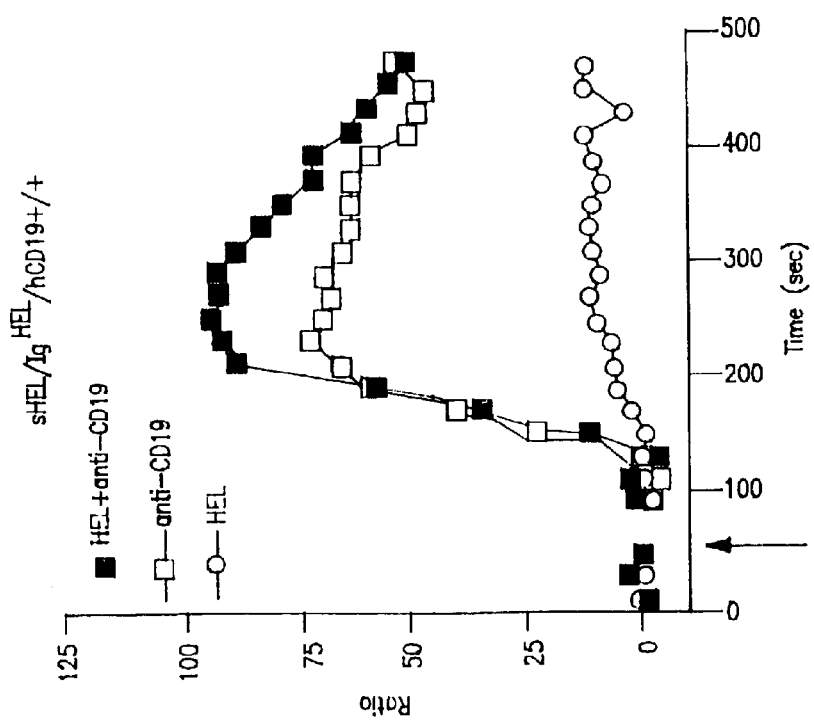

[Ca$^{++}$]$_i$ responses in B cells from sHEL/Ig$^{HEL}$/hCD19 mice. Peripheral tolerance in sHEL/Ig$^{HEL}$ mice results in the failure of anergic B cells to mobilize intracellular Ca$^{++}$ in response to HEL-mediated antigen receptor crosslinking in vitro. Cooke et al. (1994) J. Exp. Med. 179:425–438. B cells from sHEL/Ig$^{HEL}$/hCD19$^{+/+}$ mice were equivalent to anergic B cells from sHEL/Ig$^{HEL}$ mice in their failure to mobilize Ca$^{++}$ in response to HEL (FIG. 3A). B cells from sHEL/Ig$^{HEL}$/hCD19$^{+/+}$ mice that generated high levels of autoantibodies also failed to mobilize Ca$^{++}$ in response to HEL. B cells from Ig$^{HEL}$/hCD19$^{++}$ mice generated normal Ca$^{++}$ responses (FIG. 3B). Therefore, the development of autoimmunity in sHEL/Ig$^{HEL}$/hCD19$^{+/+}$ mice does not result from a CD19-induced recovery of early signaling responses in the bulk of anergic B cells.

Although antigen receptor ligation did not induce Ca$^{++}$ responses in anergic B cells, crosslinking human and mouse CD19 induced a normal C$^{++}$ response in anergic B cells from sHEL/Ig$^{HEL}$/hCD19$^{+/+}$ mice (FIG. 3A). Crosslinking mouse CD19 in sHEL/Ig$^{HEL}$ mice also induced a nominal Ca$^{++}$ response. The presence of HEL during CD19 crosslinking resulted in a Ca$^{++}$ response that was significantly greater than that observed with CD19 crosslinking alone in sHEL/Ig$^{HEL}$/hCD19$^{+/+}$ mice (P<0.01, FIG. 3A). However, the magnitude of the CD19/HEL-induced Ca$^{++}$ response in sHEL/Ig$^{HEL}$/hCD19$^{+/+}$ mice (FIG. 4A) was less than that observed in Ig$^{HEL}$/hCD19$^{+/+}$ mice (FIG. 3B). Of interest was the observation that the magnitude of the CD19-induced Ca$^{++}$ response in sHEL/Ig$^{HEL}$/hCD19$^{+/+}$ mice was always significantly higher than the Ca$^{++}$ response in Ig$^{HEL}$/hCD19$^{+/+}$ mice (n=3, p<0.05). The increased Ca$^{++}$ responses of B cells from sHEL/Ig$^{HEL}$/hCD19$^{+/+}$ mice presumably results from the endogenous ligation of antigen receptors by sHEL encountered in vivo. These results indicate that CD19 ligation can induce a relatively normal Ca$^{++}$ response in anergic B cells. Moreover, CD19 ligation can also augment transmembrane signals generated through the B-cell antigen receptor despite clonal anergy.

Thus, the striking induction of autoantibody production in sHEL/Ig$^{HEL}$ mice that are normally functionally anergic directly implicates CD19 signaling thresholds as a regulator of peripheral tolerance in B cells. CD19 overexpression by only twofold to threefold caused a breakdown of peripheral B-cell tolerance in a clear and dramatic fashion, with autoantibody levels increased several thousandfold in some sHEL/Ig$^{HEL}$/CD19$^{+/+}$ mice (FIG. 1 and 2). These dramatic increases in autoantibody levels in sHEL/Ig$^{HEL}$/hCD19$^{+/+}$ mice are even more significant given the >50% reduction in numbers of peripheral B cells in mice that overexpress CD19 (Table 1).

Overexpression of CD19 alone did not induce anergic B cells to produce autoantibodies, as evidenced by the fact that some sHEL/Ig$^{HEL}$/hCD19 mice were anergic and did not produce spontaneous autoantibodies until 5 months of age (FIG. 1). However, significant autoantibody production was induced in 2-month-old anergic sHEL/Ig$^{HEL}$/hCD19 mice by inducing inflammation with CFA (FIG. 2). Autoantibodies in sHEL/Ig$^{HEL}$ mice that overexpressed CD19 are likely to have originated from a breakdown in tolerance in conventional B cells, since HEL-specific B1a or B1b cells were not detected in Ig$^{HEL}$ (Cyster et al. (1995) *Immunity* 2:13–24), sHEL/Ig$^{HEL}$ or sHEL/Ig$^{HEL}$/hCD19 mice (Table 1). These findings suggest that alterations in CD19-related signaling thresholds breaks peripheral tolerance, which predisposes B cells to the induction of autoantibodies.

The levels of autoantibody production observed in sHEL/Ig$^{HEL}$ mice that overexpress CD19 (FIG. 1 and 2) clearly demonstrates that tolerance was abrogated in a significant portion of B cells. Since Ig$^{HEL}$ B cells are constantly exposed to antigen in transgenic sHEL mice, autoantibody production in sHEL/Ig$^{HEL}$/CD19$^{+/+}$ mice is most likely induced through an antigen receptor-dependent process. Autoantibody production in sHEL/Ig$^{HEL}$/CD19$^{+/+}$ mice may relate to the observation that CD19 ligation can augment transmembrane signals generated through the antigen receptor despite clonal anergy (FIG. 3).

Applicant has recently demonstrated that genetic alterations in CD19 expression have significant effects on the signal transduction pathways activated following B cell antigen receptor engagement. Particularly, it was shown that CD19 and CD22 reciprocally regulate Vav tyrosine phosphorylation during B lymphocyte signaling. Therefore, one pathway to autoantibody production in sHEL/Ig$^{HEL}$ mice may be via concomitant CD19 overexpression, chronic antigen receptor ligation, and the influence of inflammatory mediators triggering the simultaneous breakdown of tolerance and autoantibody production in anergic Ig$^{HEL}$ B cells.

Alternatively, inflammatory mediators such as those generated by CFA administration may induce the expansion or differentiation of antigen-stimulated Ig$^{HEL}$ B cell clones subsequent to a CD19-induced breakdown in tolerance. The latter possibility is supported by the finding that B cells from mice that overexpressed CD19 maintained a phenotype characteristic of anergic B cells and failed to generate Ca$^{++}$ responses following antigen receptor ligation (FIG. 3). The spontaneous development of autoantibodies in sHEL/Ig$^{HEL}$/hCD19 mice may also require a breakdown in T-cell tolerance, since HEL-specific helper T cells are anergic due to chronic sHEL exposure. Adelstein et al. (1991) *Science* 251:1223–1225. Thereby, soluble factors induced by CFA administration may replace the requirement for T-cell help during autoantibody production in sHEL/Ig$^{HEL}$ mice. Thus, the current results suggest strongly that inappropriate CD19 expression or function contributes to autoimmunity by disrupting tolerance.

Variability in the timing and magnitude of autoantibody production in individual sHEL/Ig$^{HEL}$/hCD19$^{+/+}$ mice is similar to what has been observed in many mouse models of autoimmunity. Theofilopoulos et al., eds. (1992) *Murine models of lupus. Systemic Lupus Erythematosus*. Churchill Livingston, Edinburgh. Overexpression of CD19 in sHEL/Ig$^{HEL}$ mice resulted in significant autoantibody production in a large portion of 2-month-old mice, while all triple-transgenic mice produced significant autoantibodies by 5 months of age (FIG. 1). The expansion and/or accumulation of B-cell clones that have escaped tolerance may explain why all sHEL/Ig$^{HEL}$/hCD19$^{+/+}$ mice produced high levels of spontaneous autoantibodies by 5 months of age. This contrasts markedly with old sHEL/Ig$^{HEL}$ mice which did not produce significant levels of anti-HEL autoantibodies (FIG. 1).

Previous studies of sHEL/Ig$^{HEL}$ mice have demonstrated that functional inactivation of autoreactive B cells is maintained throughout life. Rathmell et al. (1994) *J. Immunol.* 153:2831–2842. The variability and delayed onset of autoantibody production in sHEL/Ig$^{HEL}$/hCD19$^{+/+}$ mice may also result from their confinement to a specific-pathogen-free barrier facility. Autoantibodies first appear in some mouse models of lupus (NZB and MRL strains) around 2 months of age, but are dramatically increased by 4–5 months of age in all mice. Variability in onset and magnitude of autoantibody production also occurs in individual mice of these inbred mouse strains. Therefore, variability between the triple transgenic mice examined in this study is not surprising despite their identical genetic background and the fact that the hCD19 transgene is expressed to the same extent in all animals.

Consistent with the current studies, an association between CD19 overexpression and autoimmunity in humans has been suggested. Oooto et al. (1995) *Jpn. J. Clin. Pathol.* 43:381–384. The etiology of autoimmunity in humans has also been historically linked with the accumulation of inflammatory episodes or infectious agents and often varies in degree and time of onset. Therefore, many of the current findings in sHEL/Ig$^{HEL}$ mice mimic the evolution of autoreactive B cells and autoantibodies in humans.

In contrast with CD19 overexpressing B cells, signaling in response to antigen receptor ligation is diminished in CD45-deficient Ig$^{HEL}$ B cells. Cyster et al. (1996) *Nature* 381:325–328. Diminished signaling in CD45-deficient B cells leads to reduced negative selection in the bone marrow and prolonged retention in peripheral lymphoid tissues of mice expressing sHEL. Since the in vivo functional capacity of peripheral CD45-deficient Ig$^{HEL}$ B cells or their production of autoantibodies has not been examined, it is difficult to assess how diminished signaling in those studies relates to the results of this Example. Nonetheless, all of these studies demonstrate that antigen receptor signaling strength influences positive or negative selection, and the current studies demonstrate a direct and active role for CD19 in regulating peripheral tolerance and autoantibody generation.

For several reasons, it is unlikely that the breakdown in tolerance observed in this study results from the inadvertent insertion of the CD19 transgene into a locus that controls B cell tolerance. First, the human CD19 transgenic mice used in these studies reconstitute normal B cell function when crossed with CD19-deficient mice. Sato et al. (1997) *J. Immunol.* 158:4662–4669. The h19-1 line of mice has also been backcrossed extensively onto a wild-type C57BL/6 background without a diminution of human CD19 expression. This suggests that only one transgene integration site exists and that the heterogeneity in autoantibody production observed between triple transgenic mice does not reflect the segregated inheritance of transgenes that have integrated into multiple sites.

Applicant also has generated and analyzed 7 independent lines of hCD19 transgenic mice. Zhou et al. (1994) *Mol. Cell. Biol.* 14:3884–3894. In all cases, B cells from each mouse line demonstrate identical functional abnormalities. In lines subjected to analysis, hyper-responsive B cells and enhanced autoantibody production was observed. The magnitude of these abnormalities correlates directly and linearly with the level of hCD19 overexpression. Sato et al. (1997)

J. Immunol. 158:4662–4669. In addition, the abnormalities observed in hCD19 transgenic mice are reciprocal of what applicant has observed in CD19-deficient mice (Engel et al. (1995) *Immunity* 3:39–50; Sato et al. (1995) *Proc. Natl. Acad. Sci. USA* 92:11558–11562; Sato et al. (1996) *J. Immunol.* 156:4371–4378). Therefore, the effects observed in the current study most likely relate directly to augmented CD19 function rather than an interruption of other genes involved in tolerance regulation.

CD19 is a signaling component of a multimeric complex that includes CD21, the receptor for the C3d fragment of complement that covalently associates with antigens during complement activation. Bradbury et al. (1992) *J. Immunol.* 149:2841–2850; Matsumoto et al. (1991) *J. Exp. Med.* 173:55–64. C3d binding to CD21 can thereby act as a ligand for the CD19 complex that links complement activation with B-cell function. Pepys, M. B. (1976) *Transplant. Rev.* 32:93–120; Melchers et al. (1985) *Nature* 317:264–267; Fearon et al. (1995) *Annu. Rev. Immunol.* 13:127–149.

Since CD21-deficient mice manifest developmental and functional defects similar to those of CD19-deficient mice (Engel et al. (1995) *Immunity* 3:39–50; Rickert et al. (1995) *Nature* 376:352–355; Ahearn et al. (1996) *Immunity* 4:251–262; Molina et al. (1996) *Proc. Natl. Acad. Sci. USA* 93:3357–3361) overexpression of CD19 in vivo may mimic C3d ligation of CD21 by augmented signaling through the CD19 complex. Tedder et al. (1997) *Immunity* 6:107–118. Because the roadblock to B-cell $Ca^{++}$ responses in anergic B cells was transcended in vitro by simultaneous CD19 ligation and antigen receptor signaling (FIG. 4), C3 cleavage products binding to the CD19 complex may provide a molecular mechanism for bypassing peripheral B-cell anergy in vivo. The inappropriate or prolonged generation of C3d during inflammatory or infectious episodes in vivo may increase the responsiveness of autoreactive B cells to weak self antigens through augmented CD19 function, resulting in a breakdown of tolerance and the clonal amplification of autoantibody-producing B cells. Because altering CD19 complex function provides a mechanism for breaking self-tolerance in vivo, CD19 function may be a molecular mechanism linking inflammation with the development of autoimmune disease.

TABLE 1

Phenotype and Frequency of B lymphocytes in Lymphoid Tissues

| Tissue | Phenotype | $Ig^{HEL}$ | $Ig^{HEL}$ $hCD19^{+/+}$ | $sHEL$ $Ig^{HEL}$ | $sHEL$ $Ig^{HEL}$ $hCD19^{+/+}$ |
|---|---|---|---|---|---|
| | | Frequency (%) and Number # × $10^{-6}$) of B cells* | | | |
| bone marrow | % $IgM^-B220^{lo}$ | 14 ± 2 | 14 ± 2 | 13 ± 2 | 13 ± 2 |
| | % $IgM^+B220^{lo}$ | 32 ± 4 | 49 ± 10 | 46 ± 2 | 53 ± 3 |
| | % $IgM^+B220^{hi}$ | 16 ± 3 | 8 ± 3$^§$ | 12 ± 2 | 8 ± 1 |
| | % $HSA^{lo}B220^{hi}$ | 25 ± 3 | 9 ± 3$^1$ | 17 ± 5 | 5 ± 1$^§$ |
| blood | % $B220^+$ | 43 ± 3 | 7 ± 2$^1$ | 22 ± 3 | 6 ± 2$^1$ |
| | # $B220^+$ | 2.4 ± 0.5 | 0.3 ± 0.1$^1$ | 0.9 ± 0.2 | 0.2 ± 0.1$^1$ |
| spleen | % $B220^+$ | 36 ± 6 | 28 ± 5 | 44 ± 4 | 17 ± 3$^1$ |
| | # $B220^+$ | 24 ± 5 | 14 ± 3$^§$ | 29 ± 5 | 15 ± 6$^§$ |
| peritoneum | % $CD5^+B220^{lo}$ | 2.2 ± 0.3 | 1.3 ± 0.4 | 4.5 ± 1.1 | 1.9 ± 0.7 |
| | # $CD5^+B220^{lo}$ | 0.05 ± 0.01 | 0.05 ± 0.02 | 0.10 ± 0.02 | 0.04 ± 0.02 |
| | % $CD5^-B220^{hi}$ | 38 ± 6 | 2.7 ± 0.7$^1$ | 14 ± 2 | 1.2 ± 0.4$^1$ |
| | # $CD5^-B220^{hi}$ | 1.0 ± 0.3 | 0.07 ± 0.03$^§$ | 0.33 ± 0.03 | 0.02 ± 0.01$^1$ |

| Expression | Source of B cells | | | Levels Relative to $Ig^{HEL}$ Mice (% ± SEM)$^‡$ | | |
|---|---|---|---|---|---|---|
| IgM levels | bone | $B220^{lo}$ | 100 | 69 ± 12$^1$ | 41 ± 9 | 22 ± 8 |
| | marrow: | $B220^{hi}$ | 100 | 63 ± 4$^1$ | 4.1 ± 0.5 | 4.3 ± 0.7 |
| | blood: | $B220^+$ | 100 | 68 ± 15$^1$ | 19 ± 3 | 25 ± 4 |
| | spleen: | $B220^+$ | 100 | 62 ± 4$^1$ | 16 ± 2 | 7 ± 1$^1$ |
| I-A levels: | blood: | $IgM^+$ | 100 | 126 ± 5$^1$ | 169 ± 7 | 254 ± 33$^1$ |
| | spleen: | $IgM^+$ | 100 | 259 ± 55$^§$ | 184 ± 13 | 283 ± 30$^§$ |

* = Cumulative mean (± SEM) frequencies of different cell populations from at least five two-month-old mice of each genotype. Flow cytometry gates were used to determine the frequency of each cell type within the lymphocyte population. B-cell numbers for blood indicate the number of cells/ml. B-cell numbers from spleen and peritoneum were determined based on the total number of lymphocytes recovered.
‡ = Relative cell surface antigen densities were determined by comparing the channel numbers of mean linear fluorescence intensity between $Ig^{HEL}$ B cells and B cells from other mice. Values represent the mean expression levels obtained from at least three sets of mice of each genotype. All samples in each set of mice were stained in parallel and analyzed sequentially by flow cytometry with identical instrument settings.
$^{§17}$ = Differences between mice not expressing hCD19 and those expressing hCD19 were significant, $p < 0.05$;
$^1$ = $p < 0.01$.

EXAMPLE 2

Preparation of Monoclonal Antibodies against Prion Epitopes

As discussed above, monoclonal antibodies (mAbs) have become powerful tools in research and biotechnology. In these areas, as in the acquisition of immunity, production of potentially useful antibodies often depends on two aspects of "self"-"non-self" discrimination during the antibody response in mice. First, antibodies are not normally produced against self antigens, and secondly, antibodies to foreign antigens are normally directed exclusively at regions of the foreign antigen that differ from self. The number of monoclonal antibodies generated against species-specific antigens for use in sensitive immunoassays or allele-specific antibodies for blood grouping and tissue typing before transfusion or organ transplantation has been quite significant. However, the true potential of monoclonal antibodies has not been realized in many cases because of the difficulty in generating antibodies directed to self antigens or antigens well conserved across species barriers.

This problem has resulted in the development of a number of alternative approaches to generating monoclonal antibodies such as phage display and other in vitro approaches. While there is considerable power to these alternative approaches, the generation of dramatic antibody diversity and clonal selection of high affinity antibodies that occur normally during an immune response in animals are impossible to recapitulate in vitro. Therefore, effective methods, such as those described in Example 1, have been developed wherein clonal tolerance is blocked in vivo and wherein "self"-"non-self" discrimination is negated during the antibody response in mice. Being able to modulate the molecular basis for the cellular decision of tolerance is important for controlling the immunogenicity or tolerogenicity of vaccines, tumors, and tissue transplants, and for understanding the breakdown of self-tolerance in autoimmune diseases.

A number of molecules are key to regulating B cell function and the generation of humoral immune responses. Two examples of such molecules are CD19 and CD22. Tedder et al. (1997) *Immunity* 6:107–118; Tedder et al. (1997) *Ann. Rev. Immunol.* 15:481–504. Recent studies have demonstrated that CD19 and CD22 are members of a new class of lymphocyte surface receptors called "response regulators". This term designates that these molecules regulate the magnitude and duration of transmembrane signals received by a B lymphocyte.

Understanding how these molecules function provides multiple options for use in regulating humoral immune responses. Specifically, mice have been generated that are hyporesponsive to transmembrane signals, while other mice have been generated that are hyper-responsive to transmembrane signals. This has considerable ramifications for the abilities of these mice to recognize and generate humoral antibody responses against a variety of antigens, particularly self antigens. Moreover, this provides a powerful new approach to developing a new class of mAbs that react with molecules which are highly conserved during recent mammalian evolution.

Unconventional agents termed prion proteins (PrPsc) are considered the etiologic agent of Creutzfeldt-Jakob disease (CJD). The pathologic properties of these proteins lie in their three-dimensional configuration and their ability to recruit and influence normal PrPs to undergo similar conformational changes. Because these proteins are highly conserved across species it has been difficult to generate effective humoral immune responses against these agents in animal models.

The majority of PrPsc antigenic sites are species-directed, involve non-self sites and are common to both the normal host precursor (PrPc) and the disease form (PrPsc). Because of this, the present methods to diagnose CJD-associated diseases are lengthy, require relatively large quantities of starting material to detect PrPsc and lack sensitivity (reviewed in Kascsak et al. (1993) *Dev. Biol. Stand.* 80:141–151). See also Korth et al. (1997)(Letter to *Nature*) *Nature* 390:74.

In this Example, development of monoclonal antibodies (mAbs) reactive with PrPs is described. Development of systems for the production of mAbs reactive with distinct epitopes or conformational determinants present on PrPs but not PrPc are also described.

Determination of whether tolerance-deficient mice develop humoral immune responses to PrPc. Initial studies are initiated to determine whether tolerance-deficient mice are able to generate humoral immune responses against hamster PrPc or recombinant PrPc proteins and peptides. Mice are immunized intra-pertioneally (ip) with the test proteins and both primary and secondary humoral immune responses are assessed by ELISA. Multiple tolerance-deficient mice strains are assessed and are compared with wild-type mice of the same genetic background.

Next, different immunogens are evaluated for their ability to generate anti-PrP antibody responses to assess whether any have specific advantages. One suitable immunogen is described in Korth et al. (1997) (Letter to *Nature*) *Nature* 390:74.

Different gene-targeted or transgenic mouse models for tolerance-deficiency are then assessed to determine advantageous humoral immune responses following immunization. Upon observation of clear differences between lines of mice, then those mice with optimal humoral responses are crossed to generate a line of mice that are optimal for generating humoral responses to PrPs.

In a second wave of experiments, tolerance-deficient mice are generated that possess different major histocompatability complex (MHC) backgrounds. In many experimental models, differences in MHC genes have a predetermining effect on the ability of mice to elicit humoral immune responses. MHC differences may account for some of the difficulties in generating humoral responses to PrP protein in mice.

Currently, all tolerance-deficient mice have a C57BL/6 background. These mice are bred into a BALB/c background for at least five generations. Humoral immune responses in mice is assessed following initial crosses to assess whether this has an advantageous influence on humoral immune responses. Following these crosses, these mice are used for the generation of mAbs.

Generate mAbs Reactive with PrPc. The mice generated above and immunized with optimal antigens are used for the generation of mAbs using standard approaches, such as those described above.

A problem has been encountered in the development of hybridomas producing antibodies reactive with PrP protein in which the myeloma fusion partner cells express endogenous PrP protein which leads to the death of the hybridoma. This problem is circumvented either by genetically engineering the fusion partner myeloma cell line or introducing the appropriate genetic mutations in the mice used for fusions. These technologies will be utilized when it appears that difficulties in generating mAbs results from the above problem.

Generate mAbs with PrP0/0 tolerance-deficient mice. Mice rendered deficient in PrPc by homologous recombination gene targeting are obtained. PrP0/0 mice generate sera capable of specifically precipitating in vitro synthesized human prion proteins, while wild-type mice do not generate humoral immune responses. Drasemann et al. (1996) *J. Immunol. Methods* 199:109–118). This provides considerable advantages for generating mAbs reactive with this self-protein should responses with tolerance-deficient mice not be optimal. Furthermore, this may allow the generation of mAbs reactive with novel epitopes that may not be optimally identified in tolerance-deficient mice. PrP0/0 tolerance-deficient mice generate vigorous polyclonal immune responses after immunization with human prion gene sequences. These mice will be used as spleen donors for mAb production.

Generate mAbs reactive with "infectious" PrP isoforms. For this phase, steps are taken to adequately protect laboratory and animal care personnel against potential infectious materials. Monoclonal antibodies are then preferably generated by DNA-mediated immunization of mice, or by other standard protocols known to those in the art.

Additionally, high affinity monoclonal antibodies are prepared by the methods described in this Example. Monoclonal antibodies having high affinity for an antigen are desirable in that high affinity provides for biological activity in vivo. Some monoclonal antibodies produced by conventional methods often react with antigens in a biological sample, such as blood, but the affinity of such reactions is low.

The terms "affinity" and "high affinity" have well-recognized meanings in the art. Particularly, the term "affinity" refers to the goodness of the fit of an antigenic determinant to a single antigen-binding site, and it is independent of the number of sites. The term "high affinity" refers to a particular good fit of an antigenic determinant to a single antigen-binding site.

Typically, the affinity of an antibody and an antigenic determinant is judged by the use of an affinity constant K. Antigens (Ags) and antibodies (Abs) interact according to the reversible equilibrium equation:

$$Ag+Ab \approx AgAb$$

The affinity constant K is determined by the equation $K=[AgAb]/[Ag][Ab]$, wherein the units for K are liters per mole.

The affinity constant for a particular antigen-antibody interaction can be determined by measuring the concentration of free Ag required to fill half the antigen binding sites on the antibody. When this concentration value is plugged into the equation presented above, $K=1/[Ag]$. Thus, the reciprocal of the antigen concentration that produces half maximal binding is equal to the affinity constant of the antibody for the antigen. A high affinity antigen-antibody interaction is therefore typically described as having an affinity constant K of greater that $1\times10^5$ liters per mole. See Alberts et al. *Molecular Biology of the Cell*, Garland Publishing, Inc. (New York and London. 1983), p. 970.

Such high affinity monoclonal antibodies have application, for example, in a pharmaceutical setting. Specific binding of an antigen, such as a cancer antigen, can prevent the antigen from carrying out its biological activity in the cell with which it is associated, thereby killing the cell or slowing its growth. Alternatively, such monoclonal antibodies have application as drug carriers, for delivery of, for example, a cytotoxic agent to the cancer cell.

Production of monoclonal antibodies directed to cancer-associated antigens are also described in U.S. Pat. Nos. 5,660,834; 5,491,088; 5,665,382; 5,651,991; and 5,242,824; the entire contents of which is herein incorporated by reference.

EXAMPLE 3

Preparation of a Non-Human Animal having an Immune System with Desired Characteristics Example 1 describes breeding of transgenic mice, including a transgenic mouse which over-expresses CD19, wherein progeny of such mice possess antibody-forming cells having disrupted peripheral tolerance. Given the disclosure of Example 1, then, a practitioner having ordinary skill in the art can breed and/or prepare lines transgenic mice for cross-breeding, wherein each line of mice have immune systems with certain characteristics, to produce progeny animals having combinations of the characteristics. Such animals would be very useful, inter alia, in the preparation of monoclonal antibodies as described herein or in the preparation of vaccines. This Example describes the preparation of such an animal.

An example of a desirable characteristic is hypersensitivity to antigens so that antibodies, and particularly monoclonal antibodies, can be made against epitopes that are highly conservative among mammalian or other vertebrate species. Indeed, an animal having a hyper-sensitive immune system due to a breakdown in peripheral tolerance is described in Example 1.

In producing a non-human animal having an immune system with a predetermined or desired characteristic, it is preferable to initially prepare a transgenic animal which includes a transgene, wherein expression of the transgene in the animal imparts a predetermined or desired characteristic to a cell or a type of cells within the animal's immune system. As shown in Example 1, transgenic mice which over-express CD19 are used to provide disruption of peripheral tolerance in B lymphocytes in mice.

Preparation of transgenic animals is accomplished through use of accepted protocols in the art. Such protocols are described, for example, in Engel et al. (1995) *Immunity* 3:39–50 and in Zhou (1994) *Mol. Cell. Biol.* 14:3884–3894, wherein the production of the CD19 overexpressing transgenic mice described in Example 1 is described. Additionally, standard preparation techniques for transgenic animals, including mice, are also described in U.S. Pat. No. 5,633,076 (bovine); U.S. Pat. No. 5,573,933 (pigs); U.S. Pat. No. 5,675,063 (rabbits); U.S. Pat. No. 5,633,425 (mouse); U.S. Pat. No. 5,661,016 (mice and other animals) and U.S. Pat. No. 4,736,866 (mice and other animals), the entire contents of each of which are herein incorporated by reference.

The preferred next step in the method is to prepare a second line of transgenic animals which include a transgene, wherein expression of the transgene in the animal imparts a predetermined or desired characteristic to a cell or a type of cells within the animal's immune system. The predetermined characteristic of the cell or cells within the immune system of the second strain of transgenic animals can be the same or different from the predetermined characteristic of the cell or cells within the immune system of the first strain of animals. In Example 1, the second and subsequent lines of animals included sHEL (ML5 line) and $Ig^{HEL}$ (ML5 line) mice, as well as double transgenic sHEL/$Ig^{HEL}$ mice.

Next, the first and second strains of transgenic animals are bred according to classical breeding techniques. Such techniques are well known in the art, and are be more fully described in U.S. Pat. No. 5,633,076 (bovine); U.S. Pat. No. 5,573,933 (pigs); U.S. Pat. No. 5,675,063 (rabbits); U.S. Pat. No. 5,633,425 (mouse); U.S. Pat. No. 5,661,016 (mice and other animals) and U.S. Pat. No. 4,736,866 (mice and other animals), the entire contents of each of which are herein incorporated by reference.

Additionally, techniques for the care and breeding of a germ-free colony of mice are described in U.S. Pat. No. 5,223,410, the entire contents of which is herein incorporated by reference. Such techniques may optionally be incorporated into the production of the animal having an immune system with predetermined characteristics as described in this Example.

The resulting progeny are then screened to determine that transgenes are inherited and are subsequently expressed. Screening protocols include the well known techniques of PCR amplification, northern blot analysis and southern blot analysis using nucleic acid probes or segments from the transgene initially used to prepare the transgenic animal. Additional protocols are described in Engel et al. (1995) *Immunity* 3:39–50 and in Zhou (1994) *Mol. Cell. Biol.* 14:3884–3894.

Immune cells within the progeny are then screened to determine if the predetermined characteristics have been imparted to the cells. Such screening methods are provided in Example 1 and include isotype-specific ELISA assays and immunofluorescence assays. Finally, progeny having immune cell or cells, such as antibody-producing cells like B lymphocytes, are bred according to well-known techniques to propagate a line of mice which have within their immune systems cells which demonstrate the predetermined or desired characteristics.

In addition to the lines of mice described in of Example 1, applicant has prepared a line of CD22 deficient mice and a line of CD19 deficient mice according to standard "knockout" methods, such as those methods described in Sato et al. (1996) *Immunity* 5:551–562. The CD22 deficient line of mice exhibit a positive effect on antigen recognition, while the CD19 deficient line of mice exhibit a negative effect on antigen recognition. The lines of mice were crossed. The resulting line of mice exhibited normalized B cell development in contrast to the abnormal B cell development observed in CD22 deficient and CD19 deficient mice.

As another example of a predetermined or desired characteristic to be manipulated, the role of antigen receptor signaling strength in the development of autoreactive B cells has recently been examined in sHEL/Ig$^{HEL}$ mice. Cyster et al. (1995) *Immunity* 2:13–24; Cyster et al. (1996) *Nature (London)* 381:325–328. Mutations in the SHP1 protein tyrosine phosphatase of motheaten viable (me$^v$) mice abrogates the negative regulatory role of SHP1 in antigen receptor signaling, resulting in the generation of autoantibodies in non-transgenic mice. In Ig$^{HEL}$ mice, the me$^v$ mutation lowers signaling thresholds, which incites the negative selection of Ig$^{HEL}$ B cells in the bone marrow of sHEL mice. Cyster et al. (1995) *Immunity* 2:13–24. The SHP1 deficiency thereby prevents autoantibody generation but facilitates the development of peritoneal B1 cells reactive with HEL. Cyster et al. (1995) *Immunity* 2:13–24.

These characteristics contrast markedly with the results of Example 1, in which lowering B-cell signaling thresholds by increased CD19 expression resulted in a breakdown in tolerance and autoantibody production rather than the total negative selection of Ig$^{HEL}$ B cells in the bone marrow of sHEL mice (FIG. 1). Thus, SHP1 may play a key role in setting thresholds for negative selection in the bone marrow, while CD19 regulates peripheral tolerance. Alternately, tolerance may be finely tuned, with CD19 and SHP1 altering signaling strengths to differing extents. Thus, animals can be produced according to the methods of this Example wherein the animals have cells in their immune systems that display characteristics associated with altered SHP1 and CD19 expression.

Other examples of predetermined or desired characteristics would be apparent to one having ordinary skill in the art. See, for example, a review article by Tedder et al., entitled "The CD19-CD21 Complex Regulates Signal Transduction Thresholds Governing Humoral Immunity and Autoimmunity", *Immunity* 6:107–118 (February 1997), which discusses the role played by the CD19-CD21 complex in the immune systems of vertebrates.

The CD19 molecule forms a complex with CD21 (also known in the art as complement receptor Type II [CR2]), CD81 and Leu-13. Tedder et al. (1994) *Immunology Today* 15:437–442. Additionally, the structure and in vitro function of the CD19-CD21 complex has been characterized in the art. Tedder et al. (1994), *Immunol. Today* 15:437–442. Summarily, CD19 is a member of the immunoglobulin superfamily with a cytoplasmic region of approximately 240 amino acids. The amino acid sequences of the cytoplasmic of human CD19 (hCD19), mouse CD19 (mCD19), and guinea pig CD19 are highly homologous, which is consistent with a critical role for this region in CD19 function. CD19 physically associates with CD21 on the surface of human B cells. CD21 contains an extracellular domain of 15 or 16 repeating structural elements called short consensus repeats (SCRs), a membrane spanning region, and a 34-amino acid cytoplasmic domain. Human and mouse forms have been identified. The human form, hCD21, can physically associate with a structurally similar complement receptor, CD35 (CR1) and generate a receptor complex that does not contain CD19. The human CD35 is expressed by B cells, erythrocytes, neutrophils, monocytes, and some T cells. Thus, interactions of these molecules can be manipulated to prepare a non-human animal having an immune system with predetermined or desired characteristics associated with such a manipulation.

CD19 also associates directly with CD81, a member of the tetrospans family of proteins that includes CD9, CD37, CD53, CD63 and CD82. Bradberry et al. (1992), *J. Immunol.* 149:2841–2850 and Levy et al. (1991) *J. Biol. Chem.* 266:14597–14602. CD81 is over-expressed by most B lineage cells and by a wide variety of cell types including most lymphocytes, natural killer cells, thymocytes, eosinophils, neuroblastomas, melanomas, and fibroblasts. Thus, interactions of CD19 and CD81 within the complex can be manipulated to prepare a non-human animal having an immune system with predetermined or desired characteristics associated with such a manipulation.

Further, Table 2 presents phenotypic characteristics of mice with genetically altered response regulators of B lymphocyte signal transduction. The table presents both negative and positive effects, each such effect being a potential predetermined characteristic for an animal prepared according to the methods of this Example.

TABLE 2

Phenotypic Characteristics of Mice with Genetically Altered Response Regulators of B Lymphocyte Signal Transduction

| Genotype | Conventional B Cells | CD5+/B-1 Cells |
|---|---|---|
| Negative Effects | | |
| CD19 deficient | ↓50% decrease | ↓↓80% decrease |
| CD21 deficient | Normal | ↓40% decrease |
| BTK deficient | ↓40% decrease | ↓↓↓99% decrease |
| Xid | ↓↓70% decrease | ↓↓↓99% decrease |
| Vav deficient | ↓↓~Normal | Undetectable |
| Positive Effects | | |
| CD19 Overexpressed | ↓↓70% decrease | ↑↑↑210% increase |
| SHP1 defective | ↓↓↓ | ↑↑↑ |
| CD22 deficient | ↓50% decrease in circulating B cells | ↑Increase |
| Lyn deficient | ↓50% decrease | Normal |

Arrows represent the relative effect of the genetic alteration on B cell development As shown in Table 2, additional examples include Btk-deficient mice and Xid mice with mutations in Btk both have diminished numbers of B-1 and conventional B cells. Vav-deficient mice have similar defects.

In addition to the examples set forth in Table 2, it is also optionally desirable to prepare an animal wherein the C3 or C3d binding component to the CD19-CD21 complex is depleted. It is known in the art that such a depletion leads to impaired humoral responses to T-cell dependent and some T-cell independent antigens in mice. Pepys (1974) *J. Exp. Med.*, 140:126–145.

In vivo complement depletion suppresses the production of IgG and other T-cell dependent antibody classes much more significantly than T-cell independent IgM responses. Transient depletion of C3 also completely abrogates the development of memory B cells. Klaus and Humphrey (1977) *Immunology* 33:31–40.

Complement deficiencies that effect C3 activation in humans, guinea pigs, and dogs result in diminished humoral responses to foreign antigens. See, for example, O'Neil et al., (1988) *J. Immunol.* 140:139–145. Additionally, C3- and C4-deficient mice suffer severe defects in both their primary and secondary antibody responses to T-cell dependent antigens, even at high antigen doses.

A novel C3 mRNA transcript has been identified that encodes a truncated C3 protein. Cahen-Kramer et al. (1994), *J. Exp. Med.* 180:2079–2088. Cell lines transfected with the related cDNA secrete a co-stimulatory factor that augments the proliferation of B cells in assays with macrophage-depleted mouse splenic B cells. Such a cDNA thus provides a candidate for use in the production of a transgenic animal according to the methods of this Example.

Additionally, CD20 and CD35, or CD21/35 play a role in immune response, and are thus candidates for manipulation in an animal according to the method of this Example. It has been observed that pre-treatment of mice with a mCD21/35 MAb blocks both T-cell dependent and independent immune responses in the generation of immunological memory. See, for example, Gustavsson et al. (1995) *J. Immunol.* 154:6524–6528. Chimeric mice with normal levels of CD21/35 on their follicular dendritic cells, but not on their B cells, have defects in humoral responses to antigens similar to those of CD21/35 deficient mice. Croix et al. (1996) *J. Exp. Med.* 183:1857–1864.

Additional candidates of interest include $CD5^-$ B cells and $CD5^+$ B-1 cells, given their documented role in pathogenic autoantibody responses, such as the pathogenic autoantibody responses of systemic lupus erythematosus (SLE). SLE is characterized by production of antibodies to DNA within the body in association with systemic inflammation. Shirai et al. (1991) *Clin. Immunol. Immunopathol.* 59:173–186. See also Murakami and Honjo (1995), *Immunol. Today* 16:534–539, discussing that high affinity pathogenic IgG antibodies are generally produced by $CD5^-$ B cells.

In summary, multiple response regulators govern signaling thresholds in the cells of an animal's immune system, particularly B cells. Response regulators with positive or negative effects influence signaling through the B cell antigen-receptor complex. The resulting signaling thresholds regulate negative selection in the bone marrow, the magnitude of antibody response in the periphery, autoimmunity, and peripheral tolerance. Therefore, preparing an animal having cells in its immune system with predetermined characteristics derived from manipulation of these response regulators is highly useful in the characterization of immune response, development of monoclonal antibodies, and vaccines, and in the treatment of autoimmune disorders.

Given that methods for the production of transgenic animals well-known in the art, it is believed that any animal can be utilized in the methods of this Example, including mouse, pig, rat, rabbit, guinea pig, goat, sheep, primate, and poultry, with a mouse being preferred. Additionally, by the term "transgenic", it is meant any animal having a genome altered by the hand of man in any manner. Thus, the term "transgenic" includes the insertion of desired transgene, any of the well-known "knock-in" approaches, and any of the well-known "knock-out" approaches.

Furthermore, the preparation of lines of animals having immune system cells demonstrating a predetermined or desired characteristic for use in subsequent breeding is not limited to transgenic protocols. Any suitable protocol that generates an alteration in the cells of the animal's is contemplated to be within the scope of the method of this Example. Such protocols include, among others, exposure to mutagens, as described in Cyster et al. (1995) *Immunity* 2:13–24.

EXAMPLE 4

Alteration of Immune Response to NP Hapten in Mice

C57BL/6 mice generate T cell-dependent humoral responses to the (4-hydroxy-3-nitrophenyl)acetyl (NP) hapten that are dominated by canonical antibodies composed of a single $V_H$ gene, V186.2, and λ1 light chain. Selection for this receptor is thought to be driven by its frequency and affinity. However, lowering the activation threshold of B lymphocytes by overexpression of a single cell-surface molecule, CD19, resulted in anti-NP antibodies comprising an unprecedented diverse repertoire of $V_H$ and $V_L$ rearrangements with no or few mutations. Remarkably, many exhibited affinities for NP greater than or equal to that of canonical antibodies. Thus, antigen-receptor selection is regulated by endogenous B lymphocyte signaling thresholds and not antigen receptor affinity.

The unprecedented diverse repertoire of $V_H$ and $V_L$ rearrangements presented in this Example demonstrates the flexibility and broad ranging applicability of methods of the present invention. Indeed, the ability to alter cells of the immune system in an animal is further exemplified by the detailed characterization of the unprecedented immune response to NP presented in this Example. The production of monoclonal antibodies to highly conserved epitopes and the production of a non-human animal having cells of the immune system with a predetermined characteristic in accordance with the methods of the present invention is thus further illustrated by the data presented in this Example.

Background

Despite the enormous diversity of antibodies, inbred strains of mice often respond to haptens and simple antigens by producing remarkably homogenous antibodies (Blier and Bothwell, 1988). One of the best examples is the response of C57BL/6 ($Igh^b$) mice to the (4-hydroxy-3-nitrophenyl)acetyl (NP) hapten (Imanishi and Mäkelä, 1975). C57BL/6 mice immunized with NP coupled to protein carriers generate serum antibodies which bear the normally rare λ1 light chain (Cumano and Rajewsky, 1986; Imanishi and Mäkelä, 1975; Jacob et al., 1991; Karjalainen et al., 1980; Mäkelä and Karjalainen, 1977; Reth et al., 1978; Reth et al., 1979; Weiss and Rajewsky, 1990). Immunization with carrier protein alone elicits virtually no λ1 antibody or $A1^+$ B cells. Early in the immune response (days 4–8 post-immunization) a large proportion of activated $λ1^+$ B cells express multiple D gene segments in combination with various members of the large J558 family of $V_H$ genes, including V186.2, C1H4, CH10, V23, 24.8, V102, and V583.5 (Allen et al., 1988; Bothwell et al., 1981; Jacob and Kelsoe, 1992; Jacob et al., 1993). By day 10 after immunization, the majority of λ1+ B cells express V186.2-to-DFL16.1 gene rearrangements that encode a tyrosine-rich CDR3 region with a consensus motif, YYGS (Bothwell et al., 1981; Cumano and Rajewsky, 1985; Jacob et al., 1993; McHeyzer-Williams et al., 1993; Weiss and Rajewsky, 1990). The V186.2-to-DFL16.1 heavy chain rearrangement paired with the λ1 light chain is referred to as the canonical anti-NP B cell antigen receptor (Reth et al., 1978; Reth et al., 1979).

The homogeneity of the anti-NP response in Igh$^b$ mice (Maizels and Bothwell, 1985) is mirrored in the response of BALB/c mice to phosphorylcholine (Crews et al., 1981); antibodies produced against p-azophenylarsonate in strain A mice (Pawlak et al., 1973); the 2-phenyloxazolone response in BALB/c and DBA/2 mice (Mäkelä et al., 1978); and the response of BALB/c mice to poly(Glu$^{60}$-Ala$^{30}$-Tyr$^{10}$) (Thèze and Sommé, 1979). The cause of low genetic variance in these antibody responses remains obscure. Linkage of restricted antibody responses to single VDJ gene segments or Igh alleles suggests an occasional, single best solution to antigen-complementarity that results in expansion of that B cell lineage. In this case, strain-specific differences in the repertoire of germline $V_H$ genes would regulate the antibody response. Alternatively, several investigators have suggested that restricted antibody responses are circumscribed by self-tolerance; others note that clones expressing V(D)J rearrangements that are robustly tolerant of mutational change should outgrow mutationally fragile competitors. Nonetheless, the mechanisms driving repertoire selection has remained a controversial issue. Together, these observations have suggested that the great specificity of humoral immune responses is not the consequence of highly selective clonal activation but of competitive survival and proliferation of higher affinity B cells.

Transmembrane signals generated through the B cell antigen receptor complex regulate B cell responses to antigen binding and may thereby also regulate repertoire selection. Other cell surface molecules can also modifying B cell responses to antigen. Transmembrane signals generated through the B cell antigen receptor complex and other surface receptors are critically regulated by CD19 expression (reviewed in Fearon and Locksley, 1996; Tedder et al., 1997). CD19 functions as a general regulator of B cell proliferation, differentiation, clonal expansion in the peripheral B cell pool, and of peripheral tolerance, as described above.

Whether differences in endogenous signal transduction thresholds influence repertoire selection was assessed in this Example using C57BL/6 mice with single complementary genetic alterations that result in either the loss or overexpression of the CD19 cell surface molecule. In general, B lymphocytes from CD19-deficient (CD19-KO) mice are hypo-responsive to transmembrane signals while B lymphocytes from transgenic mice that overexpress CD19 (CD19-TG) are hyper-responsive (Engel et al., 1995; Sato et al., 1995; Zhou et al., 1994). Indeed, transgenic mice with even small increases (10–25%) in CD19 receptor density on B cells exhibit quantitative changes in B cell functional capacity. Thus, CD19-deficient and CD19-overexpressing mice serve as model systems where CD19 is a general response regulator of cell-surface receptor signaling and cellular signal transduction thresholds.

To assess the contribution of antigen receptor signaling to repertoire selection, CD19-TG, CD19KO, and wildtype C57BL/6 mice were immunized with NP coupled to the T-cell-dependent antigen, chicken gamma globulin (CGG). Mice that overexpressed CD19 generated anti-NP humoral immune responses that were quantitatively similar to those of wildtype C57BL/6 mice, while CD19KO mice generated only modest responses. However, the antibody response generated by mice that overexpressed CD19 were qualitatively distinct from those of C57BL/6 controls. $V_H$ gene segment and gene family use were unprecedently diverse in CD19TG mice and none of the anti-NP antibodies produced carried λ1 light chains. Significantly, some of the atypical antibodies bound the NP hapten better than canonical antibodies predominantly generated in wild-type C57BL/6 mice. In addition, several of the anti-NP antibodies generated by CD19-TG mice were reactive with a self antigens. Thus, endogenous signaling thresholds regulate repertoire diversity and selection during B cell responses to antigen independently of change in the immunoglobulin loci.

Anti-NP Immune Responses in Mice Overexpressing CD19

CD19TG and wildtype C57BL/6 mice were immunized with $NP_{18}$-CGG to assess their humoral immune responses to NP. Serum anti-NP antibody concentrations at the time of immunization (day 0) and on subsequent days (4, 8, 10, 16, and 58) were determined by ELISA using $NP_{25}$-BSA. Values represented either mean antibody levels (±SEM) from 4–5 individual mice per time-point following immunization relative to isotype-matched anti-NP monoclonal antibodies used to generate standard curves, or represented antibody concentrations relative to control serum from a C57BL/6 mouse immunized with $NP_{18}$-CGG. CD19TG mice generated serum IgM responses quantitatively similar to those of wildtype mice, despite an overall (~80%) reduction in peripheral B cell numbers (Engel et al., 1995). IgG1 responses of CD19TG mice were ~10-fold lower than in wildtype mice. IgG2a, IgG2b, and IgG3 responses in CD19TG mice were also below those of wildtype mice. All antibody responses were of the Igh$^b$ allotype. Remarkably, λ1 antibody responses were poor in CD19TG mice, while κ$^+$ antibody responses were similar in CD19TG and wildtype mice. Therefore, the primary NP-specific antibody response in CD19TG mice is dominated by IgM and IgG1, with the vast majority of antibodies bearing light chains other than λ1.

The relative affinity/avidity of the antibody response in CD19TG mice was assessed by comparing antisera binding to highly-($NP_{25}$-BSA) or sparsely-($NP_5$-BSA) substituted NP-bovine serum albumin (BSA) substrates over a wide range of antibody concentrations as described previously (Herzenberg et al., 1980). Values represented mean (±SEM) ratios of anti-$NP_5$ versus anti-$NP_{25}$ antibody concentrations from 4–5 individual mice per time-point. In cases where anti-NP5 antibody levels were not detectable, values of 0 were used for generating means. Differences between CD19TG and wildtype mice were significant, p<0.05, at about 3 days, 10 days and 14 days after immunization for IgM; at about 11 days, 18 days and 58 days for λ1; and at about 58 days for κ.

Despite similar levels of IgM anti-NP antibodies, the primary antibody response in CD19TG mice was generally of a lower affinity compared with antiserum from wildtype mice. However, the IgG1 antibody responses in CD19TG and wildtype mice exhibited comparable affinity maturation. Again however, the λ1 antibody response was modest and this response was of lower affinity than observed in wildtype mice. It therefore appears that in response to NP, mice overexpressing CD19 generate high affinity IgG1 antibody that does not bear λ1 light chain.

The relative frequency of anti-NP antibody-producing B cells in the spleen and bone marrow of CD19TG mice was assessed using ELISpot assays. Determined values represented mean AFC numbers (±SEM) from 4–14 individual mice per time-point following immunization on day 0. Differences between CD19TG and wildtype mice were significant, p<0.05, at about days 8 and 11 for IgM in spleen, and at about day 58 for IgG1 in bone marrow.

NP-specific IgM antibody producing cells were 2- to 7-fold higher among CD19TG mouse splenocytes than among wildtype splenocytes following immunization. The frequency of IgG1 anti-NP antibody-forming cells among CD19TG splenocytes were not significantly different from wildtype controls. CD19TG mice also had consistently higher frequencies of IgM-secreting cells and lower frequencies of IgG-secreting cells among bone marrow-derived anti-NP antibody-forming cells when compared with wildtype controls. Importantly, the overall kinetics of NP-specific antibody-forming cell responses were similar in CD19TG and wildtype mice, although the long-lived memory antibody-forming cells normally found in the marrow of wildtype mice 58 days after immunization were not present in CD19TG mice. Therefore, the serum antibody responses observed in CD19TG and wildtype mice generally mirrored the antibody-forming cell responses.

Anti-NP Immune Responses in CD19KO Mice

CD19KO mice were immunized with $NP_{18}$-CGG to compare their humoral immune responses with wildtype littermates. Mean serum anti-NP antibody concentrations (±SEM) from 4–5 individual mice per time-point following immunization (day 0) were determined by ELISA using $NP_{25}$-BSA as described above. The average relative affinity of serum anti-NP antibodies was estimated by determining the mean concentration of $NP_5$-binding and $NP_{25}$-binding antibodies at each time-point by ELISA as described above. Differences between CD19KO and wildtype were significant, p<0.05, at about 3 days and 18 days after immunization for IgM; at about 18 days and 58 days for IgG1; at about 58 days for λ1; and at about 18 and 58 days for κ.

The frequency of spleen and bone marrow cells secreting anti-$NP_{25}$-binding antibody was determined by ELISpot assays as described above. Values represent mean antibody-forming cell (AFC) numbers (±SEM) from 4–5 individual mice per time-point following immunization on day 0. Differences between CD19KO and wildtype mice were significant, p<0.05, at about days 10 and 18 for IgG1 in spleen, and at about days 10, 16 and 58 for IgG1 in bone marrow.

Serum IgM and IgG1 antibody responses to NP were 10-fold and >100-fold lower in CD19KO mice than in wildtype mice. λ1- and κ-bearing antibody responses to NP were also suppressed in CD19KO mice. Affinity maturation was also delayed and reduced in CD19KO mice when compared with wildtype mice. The relative frequency of B cells producing IgG1 anti-NP antibodies in the spleens and bone marrow of CD19KO mice was markedly lower than in wildtype mice at each time point following immunization. Therefore, antibody responses to NP in CD19KO mice were markedly diminished beyond what would be expected with the overall (40–60%) reduction in peripheral B cell numbers in these mice.

Germinal Center Responses in CD19TG and CD19KO Mice

Germinal center B cell responses in CD19TG and CD19KO mice were assessed after immunization with $NP_{18}$-CGG. Histologic sections of spleen were stained with the GL7 monoclonal antibody and/or peanut agglutinin (PNA) to identify germinal center B cells (Laszlo et al., 1993; Rose et al., 1980). Antibody specific for mouse κ light chain was used to visualize the B cell zones (follicles) within the splenic white pulp. Overall, B cell follicles were smaller in CD19TG mice than in wildtype mice both before and after NP immunization. Correspondingly, T cell zones occupied a larger portion of CD19TG mouse spleens. The overall frequency of follicles was also significantly (p<0.01) lower in CD19TG mice than in wildtype mice, reflecting reduced B cell numbers in these mice.

The frequency of $PNA^+$ germinal centers within follicles of CD19TG mice increased in response to immunization, although the germinal centers were usually smaller in CD19TG mice than in wildtype controls. The frequency of germinal centers per follicle was also significantly reduced in CD19TG mice. Nonetheless, the percentage of splenic B cells induced to express the GL7 antigen was similar in CD19TG and wildtype mice as assessed by flow cytometry, although GL7 expression kinetics were delayed in CD19TG mice. However, the increase in $GL7^+$ B cells in CD19TG mice at day 16 was due to a significant number of $GL7^+$ B cells found outside of $PNA^+$ germinal centers, something not observed in C57BL/6 mice. In fact, there were relatively few $GL7^+$ B cells within the germinal centers of CD19TG mice on day 16 but there were significant numbers of $GL7^+$ cells with abundant cytoplasmic immunoglobulin clustered around the penicilliary arterioles. Thus, germinal centers form following antigen challenge of CD19TG mice but they are small in size and dissipate at a faster rate than in wildtype mice. Moreover, the germinal centers of CD19TG mice displayed different phenotypic properties than observed in wildtype mice by the dissociation of the PNA and GL7 markers. In further contrast with results obtained in normal mice, germinal centers in CD19TG mice did not contain $\lambda1^+$ B cells after immunization with NP-CGG.

The number and size of primary follicles in CD19KO mice were normal, but generated few germinal centers or $GL7^+$ B cells following NP-immunization. Similarly, $\lambda1^+$ B cells were not observed in the few germinal centers that formed in CD19KO mice after immunization with NP. Therefore, NP-immunization did not induce a significant germinal center response in CD19KO mice.

Anti-NP Antibody Diversity in CD19TG Mice

The repertoire of anti-NP antibodies elicited in CD19TG mice was examined by generating hybridomas from splenocytes of individual CD19TG mice immunized with $NP_{18}$-CGG. The hybridomas were labeled TG2, TG3, TG7, or TG18 depending on the day of splenocyte isolation post-immunization (Table 3). Splenocytes from mice boosted with $NP_{18}$-CGG on day 15 were used to generate TG18 hybridomas. The TG2, TG3, TG7 and TG18 fusions generated 164, 36, 210, and 275 hybridomas total with 3, 1, 31, and 10 monoclonal hybridoma lines isolated that secreted antibodies reactive with NP-BSA but not BSA in ELISA assays. Surprisingly, none of these hybridomas secreted λ1-bearing antibodies (Table 3).

From the TG2 and TG3 fusions, three of the four hybridomas (75%) secreted μ, κ antibody products, while one (1) produced a γ2a, κ antibody (Table 3). The relative affinities/avidities of anti-NP antibodies were determined by calculating the ratio of $NP_5$-binding antibody concentrations to $NP_{25}$-binding antibody concentrations as previously described (Herzenberg et al., 1980). The affinity threshold for IgG1 antibody binding to each NP-BSA conjugate was determined using monoclonal antibodies with known affinities for NP. The H33Lγ1 antibody (IgG1, λ1; $K_a=2.0\times10^7$ $M^{-1}$) bound equally well to both $NP_5$-BSA and $NP_{25}$-BSA conjugates (binding ratio ~1.0), whereas the B1-8γ1 monoclonal antibody (IgG1, λ1) with a $Ka=10^6$ $M^{-1}$ exhibited 5-fold lower relative binding to $NP_5$-BSA than to $NP_{25}$-BSA (ratio ~0.2). The H50Gγ1 monoclonal antibody (IgG1, λ1) with a $Ka=1.2\times10^5$ $M^{-1}$ did not bind $NP_5$-BSA at detectable levels, but bound $NP_{25}$-BSA (ratio <0.01). Based on this analysis, these anti-NP antibodies generated from CD19TG mice had relatively low affinity/avidity values for NP.

From the TG7 fusion, 22 of the 28 hybridomas studied (79%) secreted μ antibodies while the rest secreted λ1 antibodies (Table 3). None of the antibodies bore λ1 light chains, while 68% bore λ2, 21% bore λ3, and 11% bore κ light chains. The relative affinities/avidities of the TG7 antibodies were quite heterogeneous, although the IgG1 antibodies were generally of lower affinity (Table 3). By contrast, all 10 hybridomas from the TG18 fusion secreted G1, κ antibodies with affinities/avidities equal to that of the H33Lγ1/λ1 control antibody (Table 3).

Sequence Analysis of Anti-NP Antibodies from CD19TG Mice During Primary Responses The heavy chain genes of the TG2, TG3 and TG7 hybridomas were sequenced by PCR amplification of cDNA made from hybridoma RNA. Eight of 31 antibodies (26%) were encoded by VDJ rearrangements containing $V_H$ gene segments common in the anti-NP B cells of C57BL/6 mice, V186.2, V23, and C1H4 (Table 3). Three of these antibodies, TG7-14, -17, and -99, may have arisen from a common progenitor since each had identical VDJ sequences. These were the only antibodies to display canonical VDJ sequences for anti-NP antibodies with the preferred YYGS motif in CDR3 (Table 3). Two of the three V23 containing antibodies, TG7-26, and -170, also shared identical VDJ sequences. The $V_H$ regions used by all eight hybridomas were free of somatic mutations. Thus, CD19TG mice are capable of generating antibody heavy chains typical of those obtained in $Igh^b$ mice to NP, although these represented a minority of the antibodies and none of these heavy chains paired with λ1.

The remaining 74% of primary-response antibodies used $V_H$ genes not normally found in NP-specific B cells from C57BL/6 mice (Table 3). Sixteen of these antibodies used $V_H$ segments encoded by known members of the J558 family; 86.22 (1 hybridoma), G4D11 (1 hybridoma), V130 (5 hybridomas, 2 were related), 671.5 (8 related hybridomas), and C1A4 (1 hybridoma). Remarkably, the majority of $V_H$ regions did not contain somatic mutations. One anti-NP antibody, TG7-83, used a previously unidentified $V_H$ segment similar to the 5D3 gene (Kaartinen et al., 1988) of the J558 family although six nucleotide differences at the 5' end were homologous with the 186.2 $V_H$ gene sequence. This $V_H$ sequence is similar to that of the dC5 antibody from a C57BL/6 mouse (GenBank accession number AF045488) and the germline $V_H$II gene, H30, isolated from BALB/c mice (Schiff et al., 1985) and is therefore likely to represent a heretofore unidentified $V_H$ gene segment in C57BL/6 mice.

TG7 hybridomas utilized $V_H$ gene segments from the 7183, Q52 and IX gene families (Table 3). The TG7-3 antibody was encoded by a novel $V_H$7183 family member most similar to the $V_H$61-1P gene of BALB/c mice (Chukwuocha et al., 1994). A C57BL/6 $V_H$ gene that only differs from TG7-3 at four positions was identified, although these differences are unlikely to represent somatic diversification since these residues are found in other VH7183 family members of C57BL/6 mice. The TG7-50, -108, and -110 hybridomas generated unrelated antibody products using $V_H$ segments almost identical to the OX-2 gene segment, a $V_H$ Q52 family member of BALB/c mice (Lawler et al., 1987). The TG7-125 hybridoma utilized a $V_H$ region identical to the BALB/c germline OX-1 $V_H$ gene, another member of the Q52 family. The TG7-118 hybridoma utilized a $V_H$ region most homologous with the VGAM3-8 $V_H$ gene of C57BL/6 mice, an IX gene family member (Winter et al., 1985). The TG7-188 $V_H$ sequence was also 98% homologous with $V_H$ regions of two hybridomas, 5G6 and 264, from C57BL/6 mice (GenBank accession number AF045504, Nottenburg et al., 1987). The TG7-188 $V_H$ segment may therefore represent a new member of the IX gene family in C57BL/6 mice. The AGTC changes at the 5' end may represent somatic diversification since we were unable to detect similar sequences in the C57BL/6 genome. Considerable diversity in $D_H$ and $J_H$ use by all of the hybridomas was apparent (Table 3), but relatively few antibodies contained the CDR3 YYGS motif typical of anti-NP antibodies in C57BL/6 mice. All $J_H$1 sequences were of the b allotype. Thus, the antibody response in CD19TG mice was quite diverse by day 7 after primary immunization, although the hybridomas primarily used germline genes with no, or few, somatic mutations (Table 3).

Sequence Analysis of Anti-NP Antibodies from CD19TG Mice During Secondary Responses All ten hybridomas generated from the TG18 fusion produced antibodies paired with κ light chains (Table 3). One of these, TG18-43, carried a member of the J558 family, V23, bearing 2 point mutations. The TG18-161 hybridoma $V_H$ gene segment matched the V23 sequence except for 4 nucleotide differences; 3 were clustered at codons 9, 10 and 11 which were identical to the V186.2 gene. Thus, the TG18-161 heavy chain gene rearrangement may be derived from a hybrid of two well characterized $V_H$ gene segments, V23 and V186.2, or from a previously unknown J558 family member. Consistent with the second possibility is the full identity of the TG18-161 $V_H$ gene with that present in the 70.1.4 hybridoma derived from a C57BL/6 mouse (GenBank accession number AF006576). Of the remaining eight TG18 hybridomas, six were clonally related (Table 3) with $V_H$ gene segments homologous (96%) to the germline 22.1 $V_H$ gene of the J606 $V_H$ family in BALB/c mice (Brodeur and Riblet, 1984; Hartman and Rudikoff, 1984). The two remaining hybridomas, TG18-5 and TG18-259, shared identical VDJ sequences with $V_H$ segments encoded by OX2-like genes of the Q52 family. These hybridomas utilized a $V_H$ gene segment that differed from those utilized by the unrelated TG7-50, -108 and -110 hybridomas at three positions that are potential sites of hypermutation. $D_H$ and $J_H$ gene utilization was also diverse among the TG18 hybridoma set (Table 3), although none of the antibodies encoded the YYGS motif. Thus, the repertoire of the anti-NP antibody response of CD19TG mice substantially diverges from the response of wildtype $Igh^b$ mice with only 20% (2/10) of the TG18 antibodies encoded by members of the J558 $V_H$ gene family and none carried the λ1 light chain.

λ Light Chain Utilization by Anti-NP Antibodies

In contrast with the expanded $V_H$ repertoire used to generate anti-NP antibodies in CD19TG mice, there was a striking deficiency in λ1 utilization and the λ light chain repertoire was remarkably compressed (Table 3). λ2 and λ3 diversification did not occur since only two different λ light chains were used by sixteen λ-producing hybridomas. There was no evidence of junctional diversity in any of the light chains and only one mutation was found in all of the λ3 light chains. Although heavy chain gene mutations are commonly greater than ten-fold more frequent than λ mutations during anti-NP responses (Cumano and Rajewsky, 1986; Ford et al., 1994), the lack of diversity and mutations in this large panel of antibodies was unexpected.

$V_H$ Utilization by CD19KO Mice

The repertoire of anti-NP antibodies elicited in CD19KO mice was also examined by generating hybridomas from splenocytes of individual mice. CD19KO mice were immunized with $NP_{18}$-CGG on day 0, boosted on day 7, with hybridomas generated on day 10. The KO10 fusions generated 615 hybridomas total. Only six clonal hybridomas were isolated (<1%) that secreted μ, κ antibodies with low affinities/avidities for $NP_{25}$-BSA, but not BSA, in ELISA screens (Table 3). Four antibodies were encoded by non-canonical, germline $V_H$ genes of the J558 family (Table 3). Of interest, the KO10-613 antibody was encoded by a newly described member of the J558 family, L350-7 (Kasturi et al., 1994). Two identical antibodies were encoded by a new member of the IX $V_H$ gene family. Thus, there was little affinity maturation or selection for canonical sequences in CD19-deficient mice.

Affinity Analysis of Anti-NP Antibodies

Figure 4:
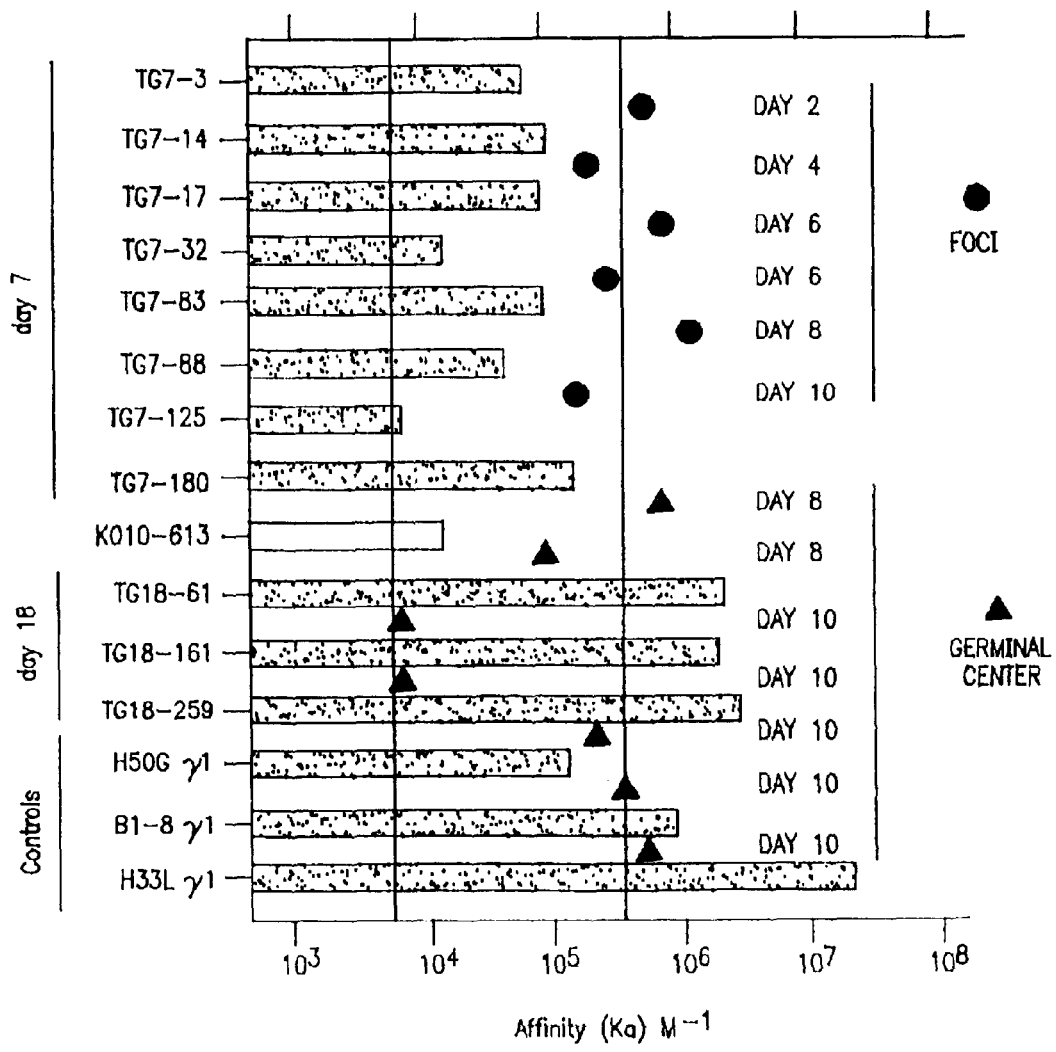
FIG. 4 depicts affinity measurements of anti-NP antibodies from hybridomas of CD19TG and CD19KO mice compared with affinities of antibodies generated wild-type C57BL/6 mice. Representative anti-NP antibodies were purified and their affinities for NP (Ka) measured by fluorescence quenching (bars). For comparison, affinities of anti-NP antibodies generated by B cells isolated from foci (filled circles) or germinal centers (filled triangles) are shown as previously described in the art. The days following NP immunization that the antibodies were isolated from mice is indicated. The thick vertical line indicates the lower limit of detection in the fluorescence quinch assay and the thin vertical line indicates the average Ka for anti-NP antibodies generated by germinal center B cells.

Antibodies representing most NP-specific hybridomas from primary and secondary responses were purified and used for NP affinity determinations by fluorescence quenching (Azuma et al., 1987; Eisen and McGuigan 1971; Jones et al., 1986). This assay measures antibody binding to NP-caproate, a monovalent derivative of the immunizing hapten. Under the conditions utilized the assay was sensitive to $7.0 \times 10^3$ $M^{-1}$, below which NP-specific binding was not detected. Of eight TG7 antibodies, the $K_a$s ranged between a low of $7.2 \times 10^3$ $M^{-1}$ for TG7-125 and a high of $1.6 \times 10^5$ $M^{-1}$ for TG7-180, with an average affinity of $7.2 \times 10^4$ $M^{-1}$ (FIG. 4). The KO10-613 antibody had a Ka of $1.3 \times 10^4$ $M^{-1}$. By contrast, all three TG18 antibodies had relatively high affinities, 1.9 to $2.9 \times 10^6$ $M^{-1}$.

The $K_a$s of the NP-specific hybridomas antibodies were also compared with $K_a$s of antibodies generated by transfectomas producing canonical anti-NP antibodies and representative antibodies utilized by B cells isolated from NP-specific foci or germinal centers according to art-recognized techniques. On average, the NP-specific antibodies generated in CD19TG mice were of lower affinity than canonical anti-NP antibodies represented by the B1-8γ1 control antibody (FIG. 4). However, the TG18 antibodies were uniformly of higher affinity than canonical antibodies or antibodies isolated from germinal centers. Thus, the CD19TG mouse generates noncanonical anti-NP antibodies of higher affinity than canonical antibodies generated in wild-type C57BL/6 mice.

B Cell Apoptosis in CD19TG and CD19KO Mice

Apoptosis regulates the immune response of B lymphocytes and influences selection for affinity maturation within germinal centers. Mice that constitutively express Bcl-$x_L$ in B cells exhibit expanded use of non-canonical anti-NP antigen receptors following immunization with NP-CGG. To assess whether decreases in apoptosis caused the dramatic shift in repertoire utilization observed in mice expressing differing CD19 levels, B cell apoptosis was assessed in situ and in vitro by two methods, TUNEL analysis and by determining the frequency of hypodiploid B cells labeled with propidium iodide. Immunohistological analysis of spleen tissue sections from CD19TG and CD19KO mice revealed that the overall frequency of apoptotic cells within follicles of each mouse strain were not obviously different from wildtype C57BL/6 littermates. The frequency of apoptotic cells in CD19KO mice was increased above C57BL/6 controls, but the majority of apoptotic cells were within the T cell zones of the knockout animals. When B cells were purified from these mice and assessed for the frequency of hypodiploid $B220^+$ B cells labeled with propidium iodide, $0.19 \pm 0.03\%$ apoptotic B cells were observed in CD19TG B cells, 0.27% in CD19KO B cells, compared with $0.20 \pm 0.03\%$ apoptotic B cells from wildtype littermates. Culturing the B cells overnight (16 h) or for 2 days in the presence of varying concentrations of anti-IgM antibodies did not reveal dramatic differences in the frequency of apoptotic cells in CD19TG mice and controls. By contrast, the frequency of apoptotic cells was significantly reduced in CD19KO B cells. Therefore, the repertoire expansion observed in CD19TG mice does not appear to result from a significantly reduced rate of B cell apoptosis.

Reactivity of Anti-NP Antibodies with Autoantigens

Figure 5A:
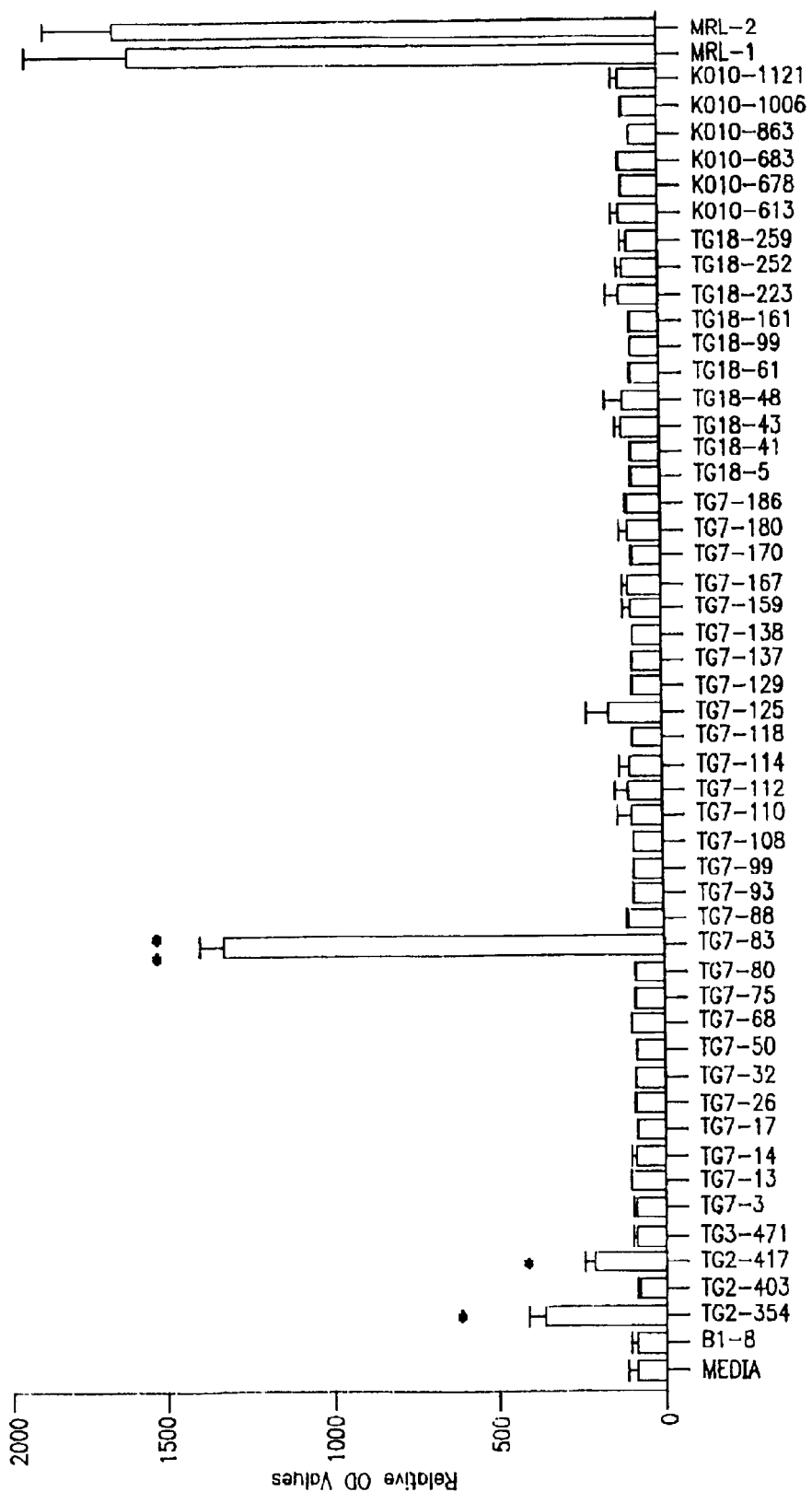
FIGS. 5A–B depicts reactivity of anti-NP antibodies with self antigens.
Figure 5B:
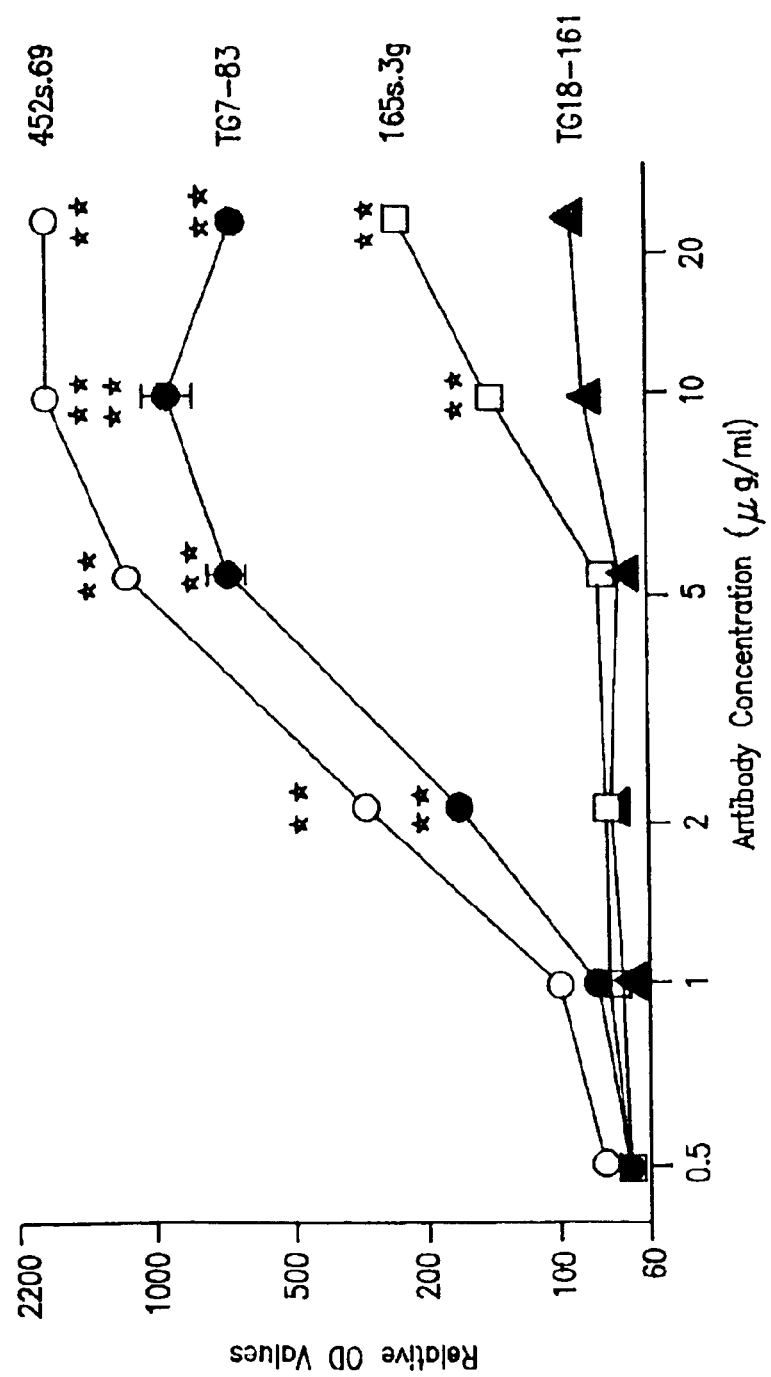

Since tolerance to self antigens may influence the diversity of the B cell repertoire and CD19TG mice have defects in peripheral tolerance, the potential for non-canonical anti-NP antibodies to react with self antigens was assessed. Of interest was that 27 of the 47 antibodies analyzed in this study had Arg residues located within their CDR3 regions compared with 12 of 45 NP-specific antibodies generated in C57BL/6 mice that were chosen randomly from the GenBank database. The facts that CD19TG mice produce anti-DNA autoantibodies and that anti-DNA autoantibodies commonly contain Arg residues within their CDR3 regions (Krishnan et al., 1995; Shlomchik et al., 1990) prompted an assessment of whether the anti-NP antibodies produced by CD19TG mice also reacted with ssDNA. The TG7-83 IgG1 antibody reacted strongly with ssDNA, at a level similar to that of serum from autoimmune $MRL^{lpr/lpr}$ mice (FIG. 5A). In fact, the relative binding of the TG7-83 antibody for ssDNA was comparable with the binding of two well-characterized, isotype-matched anti-ssDNA autoantibodies (Krishnan et al., 1995; Tillman et al., 1992) over a range of antibody concentrations (FIG. 5B). Two additional antibodies, TG2-354 and TG2-417, also bound ssDNA at levels significantly higher than non-specific control antibodies. The KO10-613, TG3-471, TG7-75, and TG7-68 antibodies also reacted with self protein antigens. This finding indicates that alterations in tolerance regulation in CD19TG mice in part account for the expanded NP-specific antibody repertoire of CD19TG mice, in accordance with the methods of the present invention.

Materials and Methods

Mice

The generation of CD19-deficient mice (CD19KO) and human CD19 (hCD19) transgenic mice (CD19TG, h19-1 line, C57BL/6) has been described in the art (Engel et al., 1995; Zhou et al., 1994). B lymphocytes of the h19-1 line of CD19TG mice express 3-fold higher levels of total cell surface CD19 (Sato et al., 1996; Sato et al., 1997) and have 9–14 copies of the hCD19 transgene integrated into a single (or closely linked) genomic site(s) on chromosome 7. The h19-1 mice used in this study were backcrossed with C57BL/6 mice (Jackson laboratory, Bar Harbor, Me.) for 8 to 10 generations without a diminution of hCD19 expression and all mice expressed similar levels of cell-surface hCD19. CD19KO mice were backcrossed with C57BL/6 mice for 8 to 10 generations. Flow cytometric analysis demonstrated that B lymphocytes from all mice expressed the $IgM^b$ but not $IgM^a$ allotype, and the mice only produce antibodies of the b allotype. All mice were 2–3 months of age at the time of use and were housed under identical conditions in a specific pathogen free barrier-facility. All studies and procedures were approved by the Animal Care and Use Committee of Duke University.

Antigens and Immunizations

Succinic anhydride esters of (4-hydroxy-3-nitrophenyl)acetyl (NP; Genosys Biotechnologies, The Woodlands, Tex.)

were reacted with CGG (Sigma Chemical Co., St. Louis, Mo.) or bovine serum albumin (BSA, Sigma Chemical Co.) as described (Jacob et al., 1991). The coupling ratio of each hapten/protein conjugate was determined spectrophotometrically. Eight-week old mice were immunized with a single intraperitoneal injection of 50 pg $NP_{18}$-CGG conjugate precipitated in alum (Jacob et al., 1991).

Quantification of Serum Anti-NP Antibody Levels

Serum IgM, IgG1, IgG2a, IgG2b, IgG3, IgA, κ light chain, and λ1 light chain antibodies specific for NP were quantified by ELISA. Wells of 96-well flat bottom plates (Costar, Cambridge, Mass.) were coated with either 5 µg/ml $NP_5$-BSA or $NP_{25}$-BSA in 0.1 M borate-buffered saline (pH 8.4) at 4° C. overnight before the wells were blocked with phosphate-buffered saline (pH 7.4) containing 2% gelatin and 1% BSA. Serially-diluted mouse sera were then added to each well at room temperature for 1.5 hours. After washing with Tris-buffered saline (pH 7.5) containing 0.05% Tween 20 (Sigma Chemical Co.), alkaline phosphatase (ALP)-labeled goat antibody specific for mouse IgM, IgG1, IgG2a, IgG2b, IgG3, IgA, or κ light chain (Southern Biotechnology Associates, Birmingham, Ala.) was added and incubated at room temperature for 1.5 hours. λ1 light chain-bearing antibody binding was assessed using biotinylated Ls136 (anti-λ1) monoclonal antibody (Reth et al., 1978) and ALP-conjugated streptavidin (Southern Biotechnology Associates). ALP activity was visualized using p-nitrophenyl phosphate substrate (Southern Biotechnology Associates) and optical densities were determined at 405 nm.

The concentrations of IgM, IgG1, λ1, or κ anti-NP antibodies were estimated by comparisons to standard curves generated using serially diluted control monoclonal antibodies on each plate. The standard for IgG1 and λ1 anti-NP antibodies was H33Lγ1, as is known in the art. The standard for IgM was B1-8, an IgM anti-NP monoclonal antibody (Reth et al., 1978). The κ antibody standard was TG18-43 (Table 3). The standard for IgG2a, IgG2b, IgG3, IgA anti-NP antibodies was serially diluted serum from a C57BL/6 mouse obtained 10 days following immunization with $NP_{18}$-CGG.

Enzyme-Linked Immunospot Assays

The frequency of NP-specific antibody-forming cells (AFC) from single-cell splenocyte and bone marrow suspensions were estimated by enzyme-linked immunospot (ELISpot) assays using $NP_5$-BSA and $NP_{25}$-BSA conjugates as has been described in the art.

Immunofluorescence Staining and Flow Cytometry Analysis

Single cell suspensions of mouse splenocytes were incubated with anti-FcgRI/RII monoclonal antibody (clone 2.4G2, PharMingen, San Diego, Calif.) for 10 min on ice to block Fcγ receptor function. To determine the frequency of $GL7^+$ cells among $B220^+$ B cells, splenocytes were subsequently incubated with FITC-labeled GL7 monoclonal antibody (PharMingen), phycoerythrin-conjugated anti-B220 monoclonal antibody (RA3-6B2, Caltag, South San Francisco, Calif.), and 7-aminoactinomycin D (Molecular Probes Inc., Eugene, Oreg.) for 30 min on ice before washing. The cells were subsequently analyzed on a FACScan flow cytometer (Becton Dickinson, San Jose, Calif.). The percentage of $GL7^+$, $B220^+$ cells was calculated from live lymphocytes selected by forward-side scatter patterns and exclusion of 7-aminoactinomycin D. In additional experiments, splenocytes were incubated with FITC-labeled anti-B220 antibody (RA3-6B2) and biotinylated Ls136 antibody, washed, and incubated with phycoerythrin-conjugated streptavidin. After washing, the frequency of $\lambda 1^+$ cells among viable $B220^+$ lymphocytes was determined by flow cytometry.

Immunohistochemistry

Six-µm-thick frozen spleen sections were mounted on poly-L-lysine (Sigma Chemical Co.)-coated slides, fixed, and stored at −80° C. as described (Jacob et al., 1991). Frozen sections were stained with horseradish peroxidase (HRP)-conjugated peanut agglutinin (PNA; ICN Pharmaceuticals, Costa Mesa, Calif.) and biotinylated Ls136 antibody, followed by streptavidin-peroxidase (Southern Biotechnology Associates) treatment as described (Jacob et al., 1991). Additional serial frozen sections were also stained with HRP-conjugated PNA and biotinylated GL7 antibody, followed by streptavidin/alkaline phosphatase, or stained with HRP-conjugated PNA and ALP-labeled anti-κ light chain antibodies. HRP and ALP activities were visualized using 3-aminoethyl carbasole (Sigma Chemical Co.) and naphthol AS-MX phosphate/fast blue BB (Sigma Chemical Co.), respectively (Jacob et al., 1991). Terminal deoxynucleotidyl transferase (TdT)-mediated dUTP-biotin nick-end labeling (TUNEL; MEBSTAIN Apoptosis kit; Immunotech, Westbrook, Me.) was used to identify apoptotic cell nuclei (Gavrieli et al., 1992) and the sections were counterstained with hematoxylin.

Hybridoma Generation

Seven to eight-week-old mice were immunized with single intraperitoneal injections of 100 µg of $NP_{18}$-CGG conjugate precipitated in alum on day 0. Two, three, or seven days after immunization, splenocytes from one or two immunized mice were fused with nonsecreting P3X63-AgB.653 myeloma cells as described (Kearney et al., 1979) and subdivided into ten 96 well tissue culture plates. One CD19TG mouse was boosted on day 15 with the same antigen and its splenocytes were fused with the myeloma cell line on day 18. Two CD19KO mice were boosted on day 7 with 100 µg of NP-CGG conjugate and their splenocytes were fused with myeloma cells on day 10. The hybridomas generated from these fusions were named based on the splenocyte source and the fusion day following immunization: for example, KO10 hybridomas were generated from splenocytes of CD19KO mice 10 days after the first immunization.

Monoclonal hybridomas secreting anti-NP antibodies were identified by ELISA. Culture supernatant fluid from each hybridoma was added to $NP_{45}$-BSA-coated 96-well flat bottom ELISA plates. After washing, ALP-labeled goat anti-mouse IgM+IgG+IgA antibodies were added to each well and ALP activity was visualized using p-nitrophenyl phosphate substrate. Hybridomas generating BSA-reactive antibodies were identified by ELISA using BSA-coated plates and were eliminated. The class and isotypes of NP-reactive antibodies were determined by ELISA with $NP_{45}$-BSA coated plates and by using mouse monoclonal antibody isotyping kits (Amersham Life Sciences, Arlington Heights, Ill.). Hybridomas secreting λ light chain antibodies were identified by ELISA using plates coated with goat anti-mouse whole Ig antibodies and ALP-labeled goat anti-mouse λ light chain antibodies (Southern Biotechnology Associates) as the developing reagent. Hybridomas secreting λ light chain antibodies were identified by immunohistochemical staining using cytospin preparations of each hybridoma. Hybridomas were centrifuged onto glass slides, dried for 2 hours, then fixed with acetone at 4° C. for 10 min. The slides were stained with biotinylated Ls136 antibody, followed by incubation with HRP-conjugated streptavidin which was visualized as above.

Some NP-specific hybridomas were grown in miniPerm bioreactors (Heraeus, South Plainfield, N.J.). Their culture supernatant fluid was concentrated and the antibody product was purified over protein G-Sepharose (Pierce, Rockford, Ill.) or mannose-binding columns (Pierce, Rockford, Ill.). Antibody protein concentrations and purity were determined by light absorption and by antibody isotype-specific sandwich ELISA.

$V_H$ and Light Chain Gene Utilization

Cytoplasmic RNA was extracted from $0.1–1\times10^6$ hybridoma cells using the RNeasy Mini Kit (Qiagen Chatsworth, Calif.). First strand cDNA was synthesized from cytoplasmic RNA using oligo-dT primers ($dT_{18}$) and a Superscript Kit (Gibco BRL, Gaitherburg, Md.). One µl of cDNA solution was used as template for PCR amplification of $V_H$ genes. PCR reactions were carried out in a 100-µl volume of a reaction mixture composed of 10 mM Tris-HCl (pH 8.3), 50 mM KCl, 1.5 mM $MgCl_2$, 200 µM dNTP (Perkin Elmer, Foster City, Calif.), 50 pmol of each primer, and 5 U of Taq DNA polymerase (ISC Bioexpress, Kaysville, Utah). Amplification was for 30 cycles (94° C. for 1 min, 58° C. for 1 min, 72° C. for 1 min; Thermocycler, Perkin Elmer). V186.2-related $V_H$ genes were amplified using a sense primer complementary to the 5' region of the V186.2 gene (primer V186.2; 5' TCTAG AATTC AGGTC CAACT GCAGC AGCC 3'—SEQ ID NO:1) and antisense primers complementary to the Cµ coding region (primer Cµ-in; 5' GAGGG GGAAG ACATT TGGGA AGGAC TG 3'—SEQ ID NO:2) or the Cγ region (primer Cγ1; 5' GAGTT CCAGG TCACT GTCAC TGGC 3'—SEQ ID NO:3). $V_H$ genes not amplified using the V186.2 primer were amplified using a promiscuous 5' $V_H$ primer (MsV$_H$E; 5' GGGAA TTCGA GGTGC AGCTG CAGGA GTCTGG 3'—SEQ ID NO:4) as previously described (Kantor et al., 1996). A light chain cDNA was amplified using a Vλ primer (5' AACTG CAGGC TGTTG TGACT CAGGA ATC—SEQ ID NO:5) and a Cλ primer (CGGGA TCCGC TCTTC AGAGG AAGGT GGAAA CA—SEQ ID NO:6). Amplified PCR products were purified from agarose gels using the QIAquick gel purification kit (Qiagen) and were sequenced directly in both directions using an ABI 377 PRISM DNA sequencer after amplification using the Perkin Elmer Dye Terminator Sequencing system with AmpliTaq DNA polymerase and the same primers for initial PCR amplification.

Sequences were compared with known $V_H$ sequences using the BLAST search program provided by the National Center for Biotechnology Information. $V_H$ genes belonging to the J558 family were analyzed as described (Bothwell et al., 1981; Gu et al., 1991).

Anti-NP Antibody Affinity Measurements

The $K_a$s of purified anti-NP antibodies was determined by fluorescence quenching as described (Azuma et al., 1987; Eisen and McGuigan, 1971; Jones et al., 1986). Briefly, $K_a$s for NP and NIP haptens were measured by fluorescence quenching in a Shimadzu RF-3501 fluorospectrophotometer (Shimadzu Scientific Instruments, Columbia, Md.). Excitation and emission wavelengths were 280 and 340 nm, respectively: temperature (25° C.) and pH (7.4) were held constant. Titration was conducted by adding NP- or NIP-caproate (Cambridge Research) over a three-log range ($10^{-8}–10^{-5}$ M) to a known concentration of antibody (33 mM in 2.5 ml PBS) in quartz cuvettes. Emission signal loss, or quench, versus antigen concentration was plotted according to the Scatchard equation to derive association constants for half-maximal binding.

Anti-ssDNA ELISA

Calf thymus DNA (Sigma Chemical Co.) was purified by repeated phenol/chloroform extraction followed by ethanol precipitation. The DNA suspension was boiled for 10 min before immersion in an ice bath to generate ssDNA. ELISA assays were carried out in 96 well Immulon II microtiter plates (Dynatech Laboratories, Chantilly, Va.) that were coated overnight at 4° C. with ssDNA (5 mg/ml in 0.1 M Na citrate buffer containing 0.15 M NaCl, pH 8.0). Plates were washed three times with PBS (pH 7.3). Supernatant fluid from individual hybridomas was diluted (generally 1:2) in PBS containing 1% BSA (Sigma) and 0.05% Tween-20 and added to triplicate wells of the antigen-coated ELISA plates. Sera from individual MRL autoimmune mice were used as positive controls which were diluted (1:100) in PBS containing 1% BSA (Sigma Chemical Co.) and 0.05% Tween-20. Peroxidase-conjugated goat anti-mouse Ig antibody diluted in PBS containing 1% BSA and 0.05% Tween-20 was added to the wells for 1 h before washing three times with PBS. Substrate solution containing 0.015% 3,3', 5,5'-tetramethylbenzidine (Sigma Chemical Co.) and 0.01% $H_2O_2$ in 0.1 M Na citrate buffer (pH 4.0) was added at room temperature for 30 min before the OD of the wells were determined at 380 nm wavelength on a Titertek Plate Reader (Flow Laboratories, McLean, Va.). OD values within the linear range of the ELISA were determined using a standard serum obtained from $MRL_{lpr/lpr}$ mice with linear regression analysis.

Assessment of Apoptosis

B cells were purified from single cell splenocyte suspensions by removing T cells with anti-Thy1.2 antibody-coated magnetic beads (Dynal, Inc., Lake Success, N.Y.). B cell suspensions were analyzed by flow cytometry following isolation to assess purity. B cell preparations from CD19KO and C57BL/6 mice were >95% $B220^+$ while preparations from CD19TG mice were >75% $B220^+$. B cells were seeded in 24-well flat bottom plates (Costar) at $1\times10^6$ cells per well with various concentration of $F(ab')_2$ fragments of goat anti-mouse IgM antibodies (Cappel, Durham, N.C.) and cultured for 16 hrs or 48 hrs in a $CO_2$ incubator. Cultured B cells were washed with PBS containing 0.2% BSA and $TUNEL^+$ cells were detected by flow cytometry analysis using the MEBSTAIN Apoptosis kit (Immunotech). The frequency of apoptotic cells was calculated: % apoptosis= [(% $TUNEL^+$ cells/(% $TUNEL^+$ cells+% live cells)]×100. Cultured cells were also washed with PBS containing 0.2% BSA followed by PBS containing 1% glucose and fixed with ice-cold 70% ethanol overnight. The fixed cells were stained with 0.05 mg/ml propidium iodide (PI; Sigma chemical Co.) solution containing 100 U/ml RNase A (Sigma Chemical Co.). Stained cells were analyzed by flow cytometry and cells with hypodiploid nuclei were considered apoptotic.

Data Analysis

All data are shown as mean values±SEM unless indicated otherwise. Analysis of variance (ANOVA) was used to analyze the data, and the Student's t test was used to compare sample means. The paired Student's t test was used to compare the means of % apoptotic cells.

TABLE 3

| Hybridoma | Isotype | $NP_{25}$ ELISA[a] | $NP_5/NP_{25}$ | $V_H$ Family | $V_{H\ gene}$[b] | Somatic Mutation | $D_H$ | $J_H$ | CDR3 Length |
|---|---|---|---|---|---|---|---|---|---|
| TG2-354 | M, κ | 0.16 | <0.01 | J558 | 86.22 | 0 | SP2.3 | 1 | 8 |
| TG2-403 | M, κ | 0.45 | <0.01 | J558 | 186.2 | 0 | SP2.2 | 2 | 7 |

TABLE 3-continued

| Hybridoma | Isotype | NP$_{25}$ ELISA[a] | NP$_5$/NP$_{25}$ | V$_H$ Family | V$_{H\ gene}$[b] | Somatic Mutation | D$_H$ | J$_H$ | CDR3 Length |
|---|---|---|---|---|---|---|---|---|---|
| TG2-417 | M, κ | 2.76 | <0.01 | J558 | G4D11 | 0 | FL16.1 | 2 | 12 |
| TG3-471 | G2a, κ | 0.17 | <0.01 | J558 | C1H4 | 0 | SP2.4/6 | 2 | 11 |
| TG7-3 | M, κ | >3.00 | <0.01 | 7183 | (61-1P) | ND[c] | ND | 3 | 5 |
| TG7-13 | M, λ2 | 2.80 | <0.01 | J558 | V23 | 0 | Q52 | 2 | 10 |
| TG7-14 | M, λ2 | >3.00 | 0.86 | J558 | 186.2 | 0 | FL16.1 | 2 | 10 |
| TG7-17 | M, λ2 | >3.00 | 0.29 | J558 | 186.2 | 0 | FL16.1 | 2 | 10 |
| TG7-26 | G1, λ2 | 1.39 | <0.01 | J558 | v23 | 0 | Q52 | 2 | 10 |
| TG7-32 | M, λ2 | >3.00 | 0.53 | J558 | 130 | 0 | FL16.1 | 2 | 10 |
| TG7-50 | M, λ2 | 2.42 | 0.42 | Q52 | OX2 | ND | Q52 | 4 | 10 |
| TG7-68 | G1, λ2 | 1.40 | <0.01 | J558 | 130 | 5 | FL16.1 | 1 | 8 |
| TG7-75 | G1, λ2 | 1.46 | <0.01 | J558 | 130 | 0 | FL16.1 | 1 | 8 |
| TG7-80 | M, λ3 | >3.00 | 1.21 | J558 | 671.5 | 0 | SP2.4/6 | 2 | 10 |
| TG7-83 | G1, λ2 | 1.43 | 0.01 | J558 | (5D3) | ND | SP2.6/7 | 3 | 5 |
| TG7-88 | M, λ2 | >3.00 | 1.31 | J558 | 671.5 | 0 | SP2.4/6 | 2 | 10 |
| TG7-93 | M, λ3 | >3.00 | 0.98 | J558 | 671.5 | 0 | SP2.4/6 | 2 | 10 |
| TG7-99 | M, λ2 | >3.00 | 0.92 | J558 | 186.2 | 0 | FL16.1 | 2 | 10 |
| TG7-108 | M, λ2 | >3.00 | 0.07 | Q52 | OX2 | ND | ST4 | 4 | 10 |
| TG7-110 | M, λ3 | >3.00 | <0.01 | Q52 | OX2 | ND | FL16.1 | 4 | 9 |
| TG7-112 | M, λ3 | >3.00 | 0.96 | J558 | 671.5 | 0 | SP2.4/6 | 2 | 10 |
| TG7-114 | M, λ2 | >3.00 | 0.45 | J558 | 130 | 0 | FL16.1 | 2 | 10 |
| TG7-118 | G1, κ | 1.20 | 0.04 | IX | (VGAM3-8) | ND | SP2.5/7 | 2 | 8 |
| TG7-125 | M, λ2 | >3.00 | 0.02 | Q52 | OX-1 | ND | SP2.9 | 4 | 8 |
| TG7-129 | M, λ3 | >3.00 | 1.04 | J558 | 671.5 | 0 | SP2.4/6 | 2 | 10 |
| TG7-137 | G1, κ | 0.99 | 0.04 | J558 | C1A4 | 0 | FL16.1 | 4 | 11 |
| TG7-138 | M, λ2 | >3.00 | 0.51 | J558 | ND | ND | ND | ND | ND |
| TG7-159 | M, λ2 | >3.00 | 1.06 | J558 | 671.5 | 0 | SP2.4/6 | 2 | 10 |
| TG7-167 | M, λ3 | >3.00 | 1.38 | J558 | 671.5 | 0 | SP2.4/6 | 2 | 10 |
| TG7-170 | M, λ2 | >3.00 | 0.05 | J558 | V23 | 0 | Q52 | 2 | 10 |
| TG7-180 | M, λ2 | >3.00 | 0.79 | J558 | 130 | 2 | FL16.1 | 1 | 12 |
| TG7-186 | M, λ2 | >3.00 | 1.01 | J558 | 671.5 | 0 | SP2.4/6 | 2 | 10 |
| TG18-5 | G1, κ | 1.45 | 0.97 | Q52 | OX2 | ND | SP2 | 4 | 7 |
| TG18-41 | G1, κ | 1.49 | 1.20 | J606 | 22.1 | ND | FL16.1 | 2 | 10 |
| TG18-43 | G1, κ | 1.35 | 0.90 | J558 | V23 | 2 | FL16.1 | 2 | 11 |
| TG18-48 | G1, κ | 1.58 | 1.14 | J606 | 22.1 | ND | FL16.1 | 2 | 10 |
| TG18-61 | G1, κ | 1.64 | 1.06 | J606 | 22.1 | ND | FL16.1 | 2 | 10 |
| TG18-99 | G1, κ | 1.64 | 0.97 | J606 | 22.1 | ND | FL16.1 | 2 | 10 |
| TG18-161 | G1, κ | 1.54 | 1.29 | J558 | (V23) | ND | Q52 | 2 | 9 |
| TG18-223 | G1, κ | 1.59 | 1.14 | J606 | 22.1 | ND | FL16.1 | 2 | 10 |
| TG18-252 | G1, κ | 1.60 | 0.82 | J606 | 22.1 | ND | FL16.1 | 2 | 10 |
| TG18-259 | G1, κ | 1.52 | 0.73 | Q52 | OX2 | ND | SP2 | 4 | 7 |
| KO10-613 | M, κ | 0.20 | <0.01 | J558 | L350-7 | ND | SP2.2-5 | 4 | 10 |
| KO10-678 | M, κ | 0.75 | 0.16 | J558 | VGAM3.0 | 0 | FL16.1 | 3 | 13 |
| KO10-683 | M, κ | 0.18 | <0.01 | IX | (VGAM3.8) | ND | FL16.1 | 3 | 10 |
| KO10-863 | M, κ | 0.55 | 0.03 | J558 | vmn2 | 0 | SP2.8 | 4 | 12 |
| KO10-1006 | M, κ | 0.48 | <0.01 | J558 | 86.22 | 1 | DST4 | 3 | 10 |
| KO10-1121 | M, κ | 0.15 | <0.01 | IX | (VGAM3.8) | ND | FL16.1 | 3 | 10 |

[a]Values represent mean ELISA OD results obtained using hybridoma culture supernatant fluid. A positive control IgM antibody (B1-8, 10 μg/ml) generated mean OD values of 1.18 while an IgG1 antibody (H33Lyl, 1.0 μg/ml) generated OD values of 1.76. All OD values were significantly greater ($p < 0.05$) than those obtained with control culture media (IgM ELISA, 0.072 ± 0.001; IgG ELISA 0.077 ± 0.001) or supernatant fluid from isotype-matched negative control hybridomas. These results are representative of those obtained in at least three experiments.
[b]Parenthesis indicate that the V$_H$ genes used are similar to those cited, but are likely to be distinct genes.
[c]ND, not determined because the homologous gene has not been identified in C57BL/6 mice, the size of the D region was too small, or there were ambiguities in the sequence of TG7-138.

References

Adelstein et al. (1991) *Science* 251:1223–1225.
Ahearn et al. (1996) *Immunity* 4:251–262.
Alberts et al. (1983) *Molecular Biology of the Cell*, Garland Publishing, Inc. (New York and London), p. 970.
Allen et al. (1988) *EMBO J.* 7:1995–2001.
Atassi, M. Z. (1980) *Molec. Cell. Biochem.* 32:21–43
Azuma et al. (1987) *Molec. Immunol.* 24:287.
Blier et al. (1988) *Immunol. Rev.* 105:27–43.
Blier et al. (1987) *J. Immunol.* 139:3996–4006.
Boersch-Supan et al. (1985) *J. Exp. Med.* 161:1272–1292.
Bothwell et al. (1981). *Cell* 24:625–637.
Bradbury et al. (1992) *J. Immunol.* 149:2841–2850.
Brodeur et al. (1984) *Eur. J. Immunol.* 14:922.
Cahen-Kramer et al. (1994), *J. Exp. Med.* 180:2079–2088.
*Cancer Treatment Reports* (1984) 68:317–328.
Carter et al. (1992) *Science* 256:105–107.
Chukwuocha et al. (1994). *Immunogenetics* 40:76–78.
Cole et al. (1985) *Monoclonal Antibodies and Cancer Therapy* 77–96.
Cooke et al. (1994) *J. Exp. Med.* 179:425–438.
Crews et al. (1981) *Cell* 25:59–66.
Croix et al. (1996) *J. Exp. Med.* 183:1857–1864.
Cumano et al. (1985) *Eur. J. Immunol.* 15:512–520.
Cumano et al. (1986) *EMBO J.* 5:2459–2466.
Cyster et al. (1996) *Nature* 381:325–328.
Cyster et al. (1995) *Immunity* 2:13–24.
Dal Porto et al. (1998) *J. Immunol.* 161 (in press).
Dempsey et al. (1996) *Science* 271:348–350.
Drasemann et al. (1996) *J. Immunol. Methods* 199:109–118.
Eisen et al. (1971) *In Methods in Immunology and Immunochemistry*, 395–411.

Engel et al. (1995) *Immunity* 3:39–50.
Fearon et al. (1996) *Science* 272:50–54.
Fearon et al. (1995) *Annu. Rev. Immunol.* 13:127–149.
Ford et al. (1994) *Eur. J. Immunol.* 24:1816-.
Gavrieli et al. (1992) *J. Cell. Biol.* 119:493–501.
Gefter et al. (1977) *Somatic Cell Genet.* 3:231–236
Goodnow et al. (1989) *Nature* 342:385–391.
Goodnow et al. (1988) *Nature* 334:676–682.
Goodnow C. C. (1992) *Annu. Rev. Immunol.* 10:489–518.
Goodnow C. C. (1996) *Proc. Natl. Acad. Sci. USA* 93:2264–2271.
Gu et al. (1991) *J. Exp. Med.* 173:1357–1371.
Gustavsson et al. (1995) *J. Immunol.* 154:6524–6528.
Hammerling et al., eds. (1981), *Monoclonal antibodies and Hybridomas*.
Hartley et al. (1991) *Nature* 353:765–769.
Hartley et al. (1993) *Cell* 72:325–335.
Hartman et al. (1984) *The EMBO J.* 3:3023–3030.
Herzenberg et al. (1980) *J. Exp. Med.* 151:1071–1087.
Howell et al. (1988) *Antibodies-A Laboratory Manual.*
Imanishi et al. (1975) *J. Exp. Med.* 141:840–854.
Inaoki et al. (1997) *J. Exp. Med.* 186:1923–1931.
Jacob et al. (1991) *J. Exp. Med.* 173:1165–1175.
Jacob et al. (1992) *J. Exp. Med.* 176:679–687.
Jacob et al. (1993) *J. Exp. Med.* 178:1293–1307.
Jones et al. (1986) *Nature* 321:522-.
Kaartinen et al. (1988) *Eur. J. Immunol.* 18:1095–1100.
Kabat et al. (1991) (Bethesda, Md.: U.S. Government Printing Office).
Kantor et al. (1996) *J. Immunol.* 158:1175–1186.
Karjalainen et al. (1980) *J. Immunol.* 125:313–317.
Kascsak et al. (1993) *Dev. Biol. Stand.* 80:141–151.
Kasturi et al. (1994) *Proc. Natl. Acad. Sci. USA* 91:8067–8071.
Kearney et al. (1979) *J. Immunol.* 123:1548–1550.
Klaus et al. (1977) *Immunology* 33:31–40.
Klinman, N. R. (1996) *Immunity* 5:189–195.
Kohler et al. (1975) *Nature* 256:495–497
Kohler et al. (1976) *Eur. J. Immunol.* 6:511–519
Korth et al. (1997) *Nature* 390:74.
Kozbor et al. (1983) *Immunology Today* 4:72.
Krishman et al. (1995) *J. Immunol.* 157:2430–2439.
Laszlo et al. (1993) *J. Immunol.* 150:5252–5262.
Lawler et al. (1987) *Proc. Natl. Acad. Sci. USA* 84:2454.
Levy et al. (1991) *J. Biol. Chem.* 266:14597–14602.
Maggio, E. T. (1980) *Enzyme-Immunoassay.*
Maizels et al. (1985) *Cell* 43:715–720.
Mason et al. (1992) *Intl. Immunol.* 4:163–175.
Matsumoto et al. (1991) *J. Exp. Med.* 173:55–64.
McHeyzer-Williams et al. (1993) *J. Exp. Med.* 178:295–305.
Melchers et al. (1985) *Nature* 317:264–267.
Miller et al. (1982) *In Hybridomas in Cancer Diagnosis and Therapy.*
Molina et al. (1996) *Proc. Natl. Acad. Sci. USA* 93:3357–3361.
Mäkelä et al. (1977) *Immunol. Rev.* 34:119–138.
Mäkelä et al. (1978) *J. Exp. Med.* 148:1644–1656.
Murakami et al. (1995) *Immunol. Today* 16:534–539.
Nemazee et al. (1989) *Nature* 337:562–566.
Nemazee et al. (1991) *Immunol. Rev.* 122:117–132.
Nottenburg et al. (1987) *J. Immunol.* 139:1718–1726.
O'Neil et al. (1988) *J. Immunol.* 140:139–145.
Oooto et al. (1995) *Jpn. J. Clin. Pathol.* 43:381–384.
Pawlak et al. (1973) *J. Exp. Med.* 137:22–31.
Pepys, M. B. (1976) *Transplant. Rev.* 32:93–120.
Pepys, M. B. (1974) *J. Exp. Med.,* 140:126–145.
Rathmell et al. (1994) *J. Immunol.* 153:2831–2842.
Reth et al. (1978) *Eur. J. Immunol.* 8:393–400.
Reth et al. (1979) *Eur. J. Immunol.* 9:1004–1013.
Rickert et al. (1995) *Nature* 376:352–355.
Rose et al. (1980) *Nature* 284:364–366.
Sato et al. (1995) *Proc. Natl. Acad. Sci. USA* 92:11558–11562.
Sato et al. (1997) *J. Immunol.* 158:4662–4669.
Sato et al. (I 996) *Immunity* 5:551–562.
Sato et al. (1996) *J. Immunol.* 156:4371–4378.
Sato et al. (1997) *J. Immunol.* 158:4662–4669.
Schiff et al. (1985) *EMBO J.* 4:1225–1230.
Schulman et al. (1978) *Nature* 276:269–270
Shirai et al. (1991) *Clin. Immunol. Immunopathol.* 59:173–186.
Shlomchik et al. (1990) *J. Exp. Med.* 171:265.
Takahashi et al. (1998) *J. Exp. Med.* 187:885–895.
Tao et al. (1990) *J. Immunol.* 145:3216–3222.
Tao et al. (1993) *Molecular Immunol.* 30:593–602.
Tedder, T. F. (1998) *Semin. Immunol.* 10:259–265.
Tedder et al. (1997) *Immunity* 6:107–118.
Tedder et al. (1994) *Immunology Today* 15:437–442.
Tedder et al. (1997) *Ann. Rev. Immunol.* 15:481–504.
Theofilopoulos et al., eds. (1992) *Murine models of lupus. Systemic Lupus Erythematosus.* Churchill Livingston, Edinburgh.
Thèze et al. (1979) *Eur. J. Immunol.* 9:294–301.
Tillman et al. (1992) *J. Exp. Med.* 176:761–779.
Turk, J. L. eds. *Research Monographs in Immunology*, Vol. 3, Elsevier/North Holland Biomedical Press, New York).
U.S. Pat. No. 3,690,834
U.S. Pat. No. 3,791,932
U.S. Pat. No. 3,817,837
U.S. Pat. No. 3,850,578
U.S. Pat. No. 3,853,987
U.S. Pat. No. 3,867,517
U.S. Pat. No. 3,901,654
U.S. Pat. No. 3,935,074
U.S. Pat. No. 3,984,533
U.S. Pat. No. 3,996,345
U.S. Pat. No. 4,098,876
U.S. Pat. No. 4,196,265
U.S. Pat. No. 4,736,866
U.S. Pat. No. 5,223,410
U.S. Pat. No. 5,242,824
U.S. Pat. No. 5,491,088
U.S. Pat. No. 5,573,933
U.S. Pat. No. 5,633,076
U.S. Pat. No. 5,633,425
U.S. Pat. No. 5,651,991
U.S. Pat. No. 5,660,834
U.S. Pat. No. 5,661,016
U.S. Pat. No. 5,665,382
U.S. Pat. No. 5,675,063
Weiss et al. (1990) *J. Exp. Med.* 172:1681–1689.
Winter et al. (1985) *EMBO J.* 4:2861–2867.
Zhou et al. (1994) *Mol. Cell. Biol.* 14:3884–3894.

---

SEQUENCE LISTING (1) GENERAL INFORMATION:
(I)      APPLICANT: TEDDER, THOMAS F.
(ii) TITLE OF INVENTION: ANTIBODY PRODUCTION METHODS RELATING TO DISRUPTION OF PERIPHERAL TOLERANCE IN B LYMPHOCYTES
(iii)    NUMBER OF SEQUENCES: 6
(iv)    CORRESPONDENCE ADDRESS:

SEQUENCE LISTING (A) ADDRESSEE: JEFFREY L. WILSON
(B) STREET: SUITE 1400, UNIVERSITY TOWER, 3100 TOWER BOULEVARD
(C) CITY: DURHAM
(D) STATE: NORTH CAROLINA
(E) COUNTRY: USA
(F) ZIP: 27707
(v) COMPUTER READABLE FORM:
(A) MEDIUM TYPE: Diskette, 3.50 inch, 1400 kB storage
(B) COMPUTER: IBM PC/XT/AT compatible
(C) OPERATING SYSTEM: Windows 95
(D) SOFTWARE: WORD PERFECT 8 and ASCII
(vi) CURRENT APPLICATION DATA:
(A) APPLICATION NUMBER: TO BE ASSIGNED
(B) FILING DATE: TO BE ASSIGNED
(C) CLASSIFICATION: TO BE ASSIGNED
(vii) PRIOR APPLICATION DATA: N/A
(A) APPLICATION NUMBER: N/A
(B) FILING DATE: N/A
(viii) ATTORNEY/AGENT INFORMATION:
(A) NAME: JEFFREY L. WILSON
(B) REGISTRATION NUMBER: 36,058
(C) REFERENCE/DOCKET NUMBER: 180/95
(ix) TELECOMMUNICATION INFORMATION:
(A) TELEPHONE: (919) 493-8000
(B) TELEFAX: (919) 419-0383
   (2) INFORMATION FOR SEQ ID NO: 1:
(I) SEQUENCE CHARACTERISTICS:
   (A) LENGTH: 29 bases
   (B) TYPE: nucleic acid
   (C) STRANDEDNESS: single
   (D) TOPOLOGY: linear
(xi) SEQUENCE DESCRIPTION: SEQ ID NO: 1:
tctagaattc aggtccaact gcagcagcc 29
   (2) INFORMATION FOR SEQ ID NO: 2:
(I) SEQUENCE CHARACTERISTICS:
   (A) LENGTH: 27 bases
   (B) TYPE: nucleic acid
   (C) STRANDEDNESS: single
   (D) TOPOLOGY: linear
(xi) SEQUENCE DESCRIPTION: SEQ ID NO: 2:
gaggggggaag acatttggga aggactg 27
   (2) INFORMATION FOR SEQ ID NO: 3:
(I) SEQUENCE CHARACTERISTICS:
   (A) LENGTH: 24 bases
   (B) TYPE: nucleic acid
   (C) STRANDEDNESS: single
   (D) TOPOLOGY: linear
(xi) SEQUENCE DESCRIPTION: SEQ ID NO: 3:
gagttccagg tcactgtcac tggc 24
   (2) INFORMATION FOR SEQ ID NO: 4:
(I) SEQUENCE CHARACTERISTICS:
   (A) LENGTH: 31 bases
   (B) TYPE: nucleic acid
   (C) STRANDEDNESS: single
   (D) TOPOLOGY: linear
(xi) SEQUENCE DESCRIPTION: SEQ ID NO: 4:
gggaattcga ggtgcagctg caggagtctg g 31
   (2) INFORMATION FOR SEQ ID NO: 5:
(I) SEQUENCE CHARACTERISTICS:
   (A) LENGTH: 28 bases
   (B) TYPE: nucleic acid
   (C) STRANDEDNESS: single
   (D) TOPOLOGY: linear
(xi) SEQUENCE DESCRIPTION: SEQ ID NO: 5:
aactgcaggc tgttgtgact caggaatc 28
   (2) INFORMATION FOR SEQ ID NO: 6:
(I) SEQUENCE CHARACTERISTICS:
   (A) LENGTH: 32 bases
   (B) TYPE: nucleic acid
   (C) STRANDEDNESS: single
   (D) TOPOLOGY: linear
(xi) SEQUENCE DESCRIPTION: SEQ ID NO: 6:
cgggatccgc tcttcagagg aaggtggaaa ca 32

It will be understood that various details of the invention may be changed without departing from the scope of the invention. Furthermore, the foregoing description is for the purpose of illustration only, and not for the purpose of limitation—the invention being defined by the claims.

---

SEQUENCE LISTING

<160> NUMBER OF SEQ ID NOS: 6

<210> SEQ ID NO 1
<211> LENGTH: 29
<212> TYPE: DNA
<213> ORGANISM: Mus sp.

<400> SEQUENCE: 1
tctagaattc aggtccaact gcagcagcc                                    29

<210> SEQ ID NO 2
<211> LENGTH: 27
<212> TYPE: DNA
<213> ORGANISM: Mus sp.

<400> SEQUENCE: 2 gaggggggaag acatttggga aggactg                                     27

<210> SEQ ID NO 3
<211> LENGTH: 24
<212> TYPE: DNA
<213> ORGANISM: Mus sp.

```
-continued

<400> SEQUENCE: 3
gagttccagg tcactgtcac tggc                                              24

<210> SEQ ID NO 4
<211> LENGTH: 31
<212> TYPE: DNA
<213> ORGANISM: Mus sp.

<400> SEQUENCE: 4
gggaattcga ggtgcagctg caggagtctg g                                      31

<210> SEQ ID NO 5
<211> LENGTH: 28
<212> TYPE: DNA
<213> ORGANISM: Mus sp.

<400> SEQUENCE: 5
aactgcaggc tgttgtgact caggaatc                                          28

<210> SEQ ID NO 6
<211> LENGTH: 32
<212> TYPE: DNA
<213> ORGANISM: Mus sp.

<400> SEQUENCE: 6
cgggatccgc tcttcagagg aaggtggaaa ca                                     32
```

What is claimed is:

1. A method for producing a monoclonal antibody specific for an antigen, the method comprising:
   (a) providing a transgenic mouse whose genome comprises a DNA sequence encoding a CD19 operably linked to a promoter and overexpressing CD19 in antibody-producing cells, wherein said antibody-producing cells have disrupted peripheral tolerance;
   (b) immunizing said transgenic mouse with an antigen to permit said antibody-producing cells to produce antibodies to the antigen, wherein said antigen is selected from the group consisting of an autoantigen and a highly conserved antigen:
   (c) removing at least a portion of said antibody-producing cells from the mouse;
   (d) forming a hybridoma by fusing one of the antibody-producing cells with an immortalizing cell wherein the hybridoma is capable of producing a monoclonal antibody to the antigen;
   (e) propagating the hybridoma; and
   (f) harvesting the monoclonal antibodies produced by the hybridoma.

2. The method of claim 1, wherein said monoclonal antibodies comprise antibodies having an affinity constant of greater than $1 \times 10^5$ liters per mole for said antigen.

* * * * *